(12) United States Patent
Shini et al.

(10) Patent No.: US 12,065,699 B2
(45) Date of Patent: Aug. 20, 2024

(54) MONITORING AND DIAGNOSIS FOR IMMUNOTHERAPY, AND DESIGN FOR THERAPEUTIC AGENT

(71) Applicant: Repertoire Genesis Incorporation, Ibaraki (JP)

(72) Inventors: Tadasu Shini, Shizuoka (JP); Ryuji Suzuki, Tokyo (JP)

(73) Assignee: Repertoire Genesis Incorporation, Ibaraki (JP)

( * ) Notice: Subject to any disclaimer, the term of this patent is extended or adjusted under 35 U.S.C. 154(b) by 1034 days.

(21) Appl. No.: 16/085,455

(22) PCT Filed: Mar. 14, 2017

(86) PCT No.: PCT/JP2017/010218
§ 371 (c)(1),
(2) Date: Sep. 14, 2018

(87) PCT Pub. No.: WO2017/159686
PCT Pub. Date: Sep. 21, 2017

(65) Prior Publication Data
US 2019/0080044 A1    Mar. 14, 2019

(30) Foreign Application Priority Data

Mar. 15, 2016   (JP) ................................. 2016-050861

(51) Int. Cl.
*C12Q 1/6881* (2018.01)
*C07K 7/04* (2006.01)
(Continued)

(52) U.S. Cl.
CPC .............. *C12Q 1/6881* (2013.01); *C07K 7/04* (2013.01); *G01N 33/574* (2013.01);
(Continued)

(58) Field of Classification Search
None
See application file for complete search history.

(56) References Cited

U.S. PATENT DOCUMENTS

2002/0085997 A1    7/2002 Schmidt et al.

FOREIGN PATENT DOCUMENTS

| JP | 2000-506125 A | 5/2000 |
| JP | 2015-533473 A | 11/2015 |

(Continued)

OTHER PUBLICATIONS

Overwijk et al. Mining the mutanome: developing highly personalized Immunotherapies based on mutational analysis of tumors Hournal for ImmunoTherapy of Cancer vol. 1, article 11 (Year: 2013).*

(Continued)

*Primary Examiner* — Larry D Riggs, II
*Assistant Examiner* — Mary C Leverett
(74) *Attorney, Agent, or Firm* — Seed IP Law Group LLP

(57) ABSTRACT

The present invention provides a method for producing a peptide for the treatment (in particular, immunotherapy), monitoring, or diagnosis of a disease in a subject. This method is achieved by obtaining information pertaining to a genome read, for example an exome read, of the subject and a mutation thereof, and, as necessary, information regarding the RNA sequence of the subject and information regarding the MHC type of the subject, analyzing an epitope related to the mutation on the basis of the information pertaining to the genome read (for example, the exome read) and the mutation, arbitrary information from the RNA sequence, the MHC type information, and information regarding the disease, and producing a peptide, as necessary, on the basis of information regarding the epitope.

8 Claims, 7 Drawing Sheets

Specification includes a Sequence Listing.

(51) Int. Cl.

| | | |
|---|---|---|
| *G01N 33/574* | (2006.01) | |
| *G01N 33/68* | (2006.01) | |
| *G16B 5/00* | (2019.01) | |
| *G16B 5/20* | (2019.01) | |
| *G16B 15/00* | (2019.01) | |
| *G16B 15/30* | (2019.01) | |
| *G16B 20/00* | (2019.01) | |
| *G16B 20/20* | (2019.01) | |
| *G16B 20/30* | (2019.01) | |
| *G16B 25/10* | (2019.01) | |
| *G16B 30/00* | (2019.01) | |
| *G16B 30/10* | (2019.01) | |
| *G16B 40/00* | (2019.01) | |
| *G16B 45/00* | (2019.01) | |
| *G16B 50/10* | (2019.01) | |
| *G16B 50/20* | (2019.01) | |

(52) U.S. Cl.
CPC ............ *G01N 33/6878* (2013.01); *G16B 5/00* (2019.02); *G16B 5/20* (2019.02); *G16B 15/00* (2019.02); *G16B 15/30* (2019.02); *G16B 20/00* (2019.02); *G16B 20/20* (2019.02); *G16B 20/30* (2019.02); *G16B 25/10* (2019.02); *G16B 30/00* (2019.02); *G16B 30/10* (2019.02); *G16B 40/00* (2019.02); *G16B 45/00* (2019.02); *G16B 50/10* (2019.02); *G16B 50/20* (2019.02); *C12Q 2600/156* (2013.01)

(56) References Cited

FOREIGN PATENT DOCUMENTS

| JP | 2016-501870 | A | 1/2016 | | |
|---|---|---|---|---|---|
| WO | 2014/012051 | A1 | 1/2014 | | |
| WO | WO-2014052707 | A2 | * 4/2014 | ......... | A61K 39/0011 |
| WO | 2014/082729 | A1 | 6/2014 | | |
| WO | 2014/180490 | A1 | 11/2014 | | |
| WO | 2015/103037 | A2 | 7/2015 | | |

OTHER PUBLICATIONS

Pedersen et al. Instruments for Automated Peptide Synthesis Methods in Molecular Biology vol. 1047,j pp. 215-224 (Year: 2013).*
Shendure et al. Next-generation DNA sequencing Nature Biotechnology vol. 26, pp. 1135-1145 (Year: 2008).*
Nezafat, N., Ghasemi, Y., Javadi, G., Khoshnoud, M. J., & Omidinia, E. (2014). A novel multi-epitope peptide vaccine against cancer: an in silico approach. Journal of theoretical biology, 349, 121-134. (Year: 2014).*
Lu et al., "Cancer immunotherapy targeting neoantigens," *Seminars in Immunology* 28:22-27, 2016.
Gubin et al., "Tumor neoantigens: building a framework for personalized cancer immunotherapy," *The Journal of Clinical Investigation* 125(9):3413-3421, 2015.
Hacohen et al., "Getting Personal with Neoantigen-Based Therapeutic Cancer Vaccines," *Cancer Immunol Res* 1(1):OF1-OF5, 2013 (6 pages).
Hundal et al., "pVAC-Seq: A genome-guided in silico approach to identifying tumor neoantigens," *Genome Medicine* 8:11, 2016 (12 pages).
Karasaki et al., "Identification of Individual Cancer-Specific Somatic Mutations for Neoantigen-Based Immunotherapy of Lung Cancer," *Journal of Thoracic Oncology* 11(3):324-333, 2016.
Kreiter et al., "Mutant MHC class II epitopes drive therapeutic immune responses to cancer," *Nature* 520:692-696, 2015 (18 pages).
Nielsen et al., "Toward Personalized Lymphoma Immunotherapy: Identification of Common Driver Mutations Recognized by Patient CD8+ T Cells," *Clin Cancer Res* 22(9):2226-2236, 2015 (12 pages).
Rajasagi et al., "Systematic identification of personal tumor-specific neoantigens in chronic lympocytic leukemia," *Blood* 124(3):453-462, 2014.
Shiina, "Next generation sequencing based HLA genomic and polymorphism analyses," *Major Histocompatibility Complex* 22(2): 84-94, 2015, (with partial English translation), 17 pages.
Castle et al., "Exploiting the Mutanome for Tumor Vaccination," *Cancer Res.* 72(5):1081-1091, Jan. 2012.
Decision of Rejection, dated Apr. 29, 2022, for Chinese Application No. 201780024830.X, 8 pages. (with English Translation).
Dellaire, Ph.D., Graham, et al. (eds.), *Cancer Genomics: From Bench to Personalized Medicine*, Elsevier Inc., 2014. (472 pages).
Communication pursuant to Article 94(3) EPC for European Application No. 17 766 684.9, dated May 6, 2024, 7 pages.
Yadav et al., "Predicting immunogenic tumour mutations by combining mass spectrometry and exome sequencing," Nature, vol. 515, Nov. 27, 2014, 16 pages.

* cited by examiner

New Analysis (No Template)

1. target read files
2. reads trimming
3. analysis
   comment

3. analysis

3.1. exome mapping and mutation search
- mapping algorithm: bwa mem
- band width: 10
- max edit distance:
- other options:

3.2. RNA-seq mapping and expression analysis
- segment length: 16
- read mismatch: 2
- read gap length: 2
- read edit distance: 2
- other TopHat options:
- ☑ use RefSeq as guide gene models
- other CuffLinks options:

3.3. mutation detection
- ☑ muTect      ☑ LoFreq
- ☑ VarScan     ☐ GATK

3.4. annotation to mutations
- ☑ refGene(refGene)            ☑ cosmic DB(cosmic70)
- ☑ knownGene(knownGene)        ☑ 1000 genomes(1000g2014oct)
- ☑ ensGene(ensGene)            ☑ dbSNP(snp138)
- ☑ whole exome features(jb26_all)

3.5. HLA typing
- ☑ exec
- other opttype options:

3.6. epitope prediction
- method: NetMHCpan
- specific allele list:
- up/downstream peptide margin: 13
- epitope length: 8 - 14

Save Template         Register    Cancel

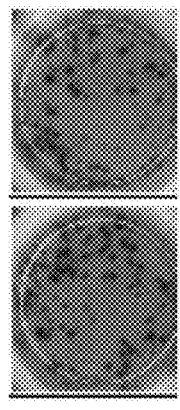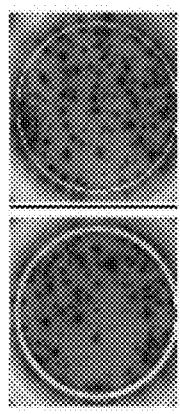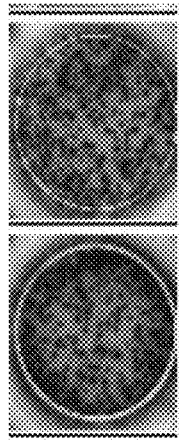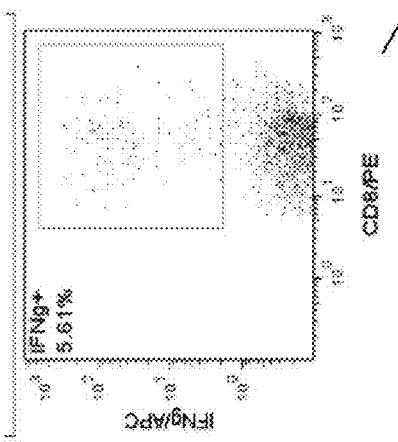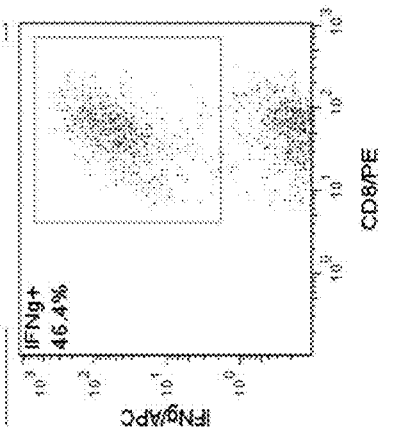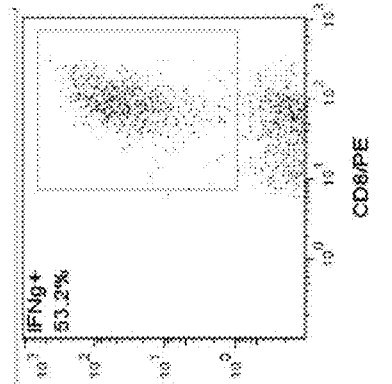
FIG.6

```
                        SEQUENCE LISTING

<160> NUMBER OF SEQ ID NOS: 36

<210> SEQ ID NO 1
<211> LENGTH: 12
<212> TYPE: PRT
<213> ORGANISM: artificial sequence
<220> FEATURE:
<223> OTHER INFORMATION: 1st sample WT peptide

<400> SEQUENCE: 1

Leu Ala Asn Phe Val Leu Gln Asp Gln Leu Ala Leu
1               5                   10

<210> SEQ ID NO 2
<211> LENGTH: 8
<212> TYPE: PRT
<213> ORGANISM: artificial sequence
<220> FEATURE:
<223> OTHER INFORMATION: 2nd sample WT peptide

<400> SEQUENCE: 2

Ile Ala Gln Arg Ser Val Thr Leu
1               5

<210> SEQ ID NO 3
<211> LENGTH: 12
<212> TYPE: PRT
<213> ORGANISM: artificial sequence
<220> FEATURE:
<223> OTHER INFORMATION: 3rd sample WT peptide

<400> SEQUENCE: 3

Thr Tyr Pro Ala Ala His His Phe Arg Ile Gly Ile
1               5                   10

<210> SEQ ID NO 4
<211> LENGTH: 12
<212> TYPE: PRT
<213> ORGANISM: artificial sequence
<220> FEATURE:
<223> OTHER INFORMATION: 1st sample MT peptide

<400> SEQUENCE: 4

Phe Ala Asn Phe Val Leu Gln Asp Gln Leu Ala Leu
1               5                   10

<210> SEQ ID NO 5
<211> LENGTH: 8
<212> TYPE: PRT
<213> ORGANISM: artificial sequence
<220> FEATURE:
<223> OTHER INFORMATION: 2nd sample MT peptide
```

```
<400> SEQUENCE: 5

Ile Ala Leu Arg Ser Val Thr Leu
1               5

<210> SEQ ID NO 6
<211> LENGTH: 12
<212> TYPE: PRT
<213> ORGANISM: artificial sequence
<220> FEATURE:
<223> OTHER INFORMATION: 3rd sample MT peptide

<400> SEQUENCE: 6

Thr Tyr Pro Ala Ala His His Phe Arg Ser Gly Ile
1               5                   10

<210> SEQ ID NO 7
<211> LENGTH: 13
<212> TYPE: PRT
<213> ORGANISM: artificial sequence
<220> FEATURE:
<223> OTHER INFORMATION: 1st sample upstream AA

<400> SEQUENCE: 7

Ile Tyr Phe Gly Thr Ala Tyr Val Ala Leu Thr Arg Asp
1               5                   10

<210> SEQ ID NO 8
<211> LENGTH: 13
<212> TYPE: PRT
<213> ORGANISM: artificial sequence
<220> FEATURE:
<223> OTHER INFORMATION: 2nd sample upstream AA

<400> SEQUENCE: 8

Arg Lys Pro Cys Asp Asn Gly Asp Pro Tyr Val Ile Ala
1               5                   10

<210> SEQ ID NO 9
<211> LENGTH: 13
<212> TYPE: PRT
<213> ORGANISM: artificial sequence
<220> FEATURE:
<223> OTHER INFORMATION: 3rd sample upstream AA

<400> SEQUENCE: 9

Lys Leu Ser Pro Thr Tyr Pro Ala Ala His His Phe Arg
1               5                   10

<210> SEQ ID NO 10
<211> LENGTH: 13
<212> TYPE: PRT
<213> ORGANISM: artificial sequence
<220> FEATURE:
<223> OTHER INFORMATION: 1st sample downstream AA

<400> SEQUENCE: 10

Ala Asn Phe Val Leu Gln Asp Gln Leu Ala Leu Asp Leu
1               5                   10

<210> SEQ ID NO 11
<211> LENGTH: 13
<212> TYPE: PRT
<213> ORGANISM: artificial sequence
<220> FEATURE:
<223> OTHER INFORMATION: 2nd sample downstream AA

<400> SEQUENCE: 11
```

```
Arg Ser Val Thr Leu Pro Thr His Arg Glu Thr Pro Glu
1               5                   10

<210> SEQ ID NO 12
<211> LENGTH: 13
<212> TYPE: PRT
<213> ORGANISM: artificial sequence
<220> FEATURE:
<223> OTHER INFORMATION: 3rd sample downstream AA

<400> SEQUENCE: 12

Gly Ile Ile Gly Ser Gly Leu Cys Val Phe Ser Lys His
1               5                   10

<210> SEQ ID NO 13
<211> LENGTH: 10
<212> TYPE: PRT
<213> ORGANISM: artificial sequence
<220> FEATURE:
<223> OTHER INFORMATION: pepID 14 MT

<400> SEQUENCE: 13

Phe Leu Ala Leu Glu Cys Leu Ala His Leu
1               5                   10

<210> SEQ ID NO 14
<211> LENGTH: 10
<212> TYPE: PRT
<213> ORGANISM: artificial sequence
<220> FEATURE:
<223> OTHER INFORMATION: pepID 21 MT

<400> SEQUENCE: 14

Gln Leu Leu Glu Pro Glu Ile Ser Phe Leu
1               5                   10

<210> SEQ ID NO 15
<211> LENGTH: 9
<212> TYPE: PRT
<213> ORGANISM: artificial sequence
<220> FEATURE:
<223> OTHER INFORMATION: pepID 41 MT

<400> SEQUENCE: 15

Phe Thr Tyr Ser Ser Ala Leu Lys Val
1               5

<210> SEQ ID NO 16
<211> LENGTH: 10
<212> TYPE: PRT
<213> ORGANISM: artificial sequence
<220> FEATURE:
<223> OTHER INFORMATION: pepID 36 MT

<400> SEQUENCE: 16

Ile Leu Gln Glu Tyr Arg Glu Asp Phe Val
1               5                   10

<210> SEQ ID NO 17
<211> LENGTH: 10
<212> TYPE: PRT
<213> ORGANISM: artificial sequence
<220> FEATURE:
<223> OTHER INFORMATION: pepID 7 MT

<400> SEQUENCE: 17
```

```
Val Leu Asn Ile Asn Asp Asn Glu Pro Val
1               5                   10

<210> SEQ ID NO 18
<211> LENGTH: 10
<212> TYPE: PRT
<213> ORGANISM: artificial sequence
<220> FEATURE:
<223> OTHER INFORMATION: pepID 43 MT

<400> SEQUENCE: 18

Phe Gln Tyr Ser Ser Pro Ala Leu Pro Thr
1               5                   10

<210> SEQ ID NO 19
<211> LENGTH: 9
<212> TYPE: PRT
<213> ORGANISM: artificial sequence
<220> FEATURE:
<223> OTHER INFORMATION: pepID 30 MT

<400> SEQUENCE: 19

Ala Leu Tyr Pro Phe Glu Phe Arg Ser
1               5

<210> SEQ ID NO 20
<211> LENGTH: 9
<212> TYPE: PRT
<213> ORGANISM: artificial sequence
<220> FEATURE:
<223> OTHER INFORMATION: pepID 33 MT

<400> SEQUENCE: 20

Asn Ile Ser Ser Arg Ile His Thr Val
1               5

<210> SEQ ID NO 21
<211> LENGTH: 9
<212> TYPE: PRT
<213> ORGANISM: artificial sequence
<220> FEATURE:
<223> OTHER INFORMATION: pepID 42 MT

<400> SEQUENCE: 21

Lys Thr Phe Thr Tyr Ser Ser Ala Leu
1               5

<210> SEQ ID NO 22
<211> LENGTH: 10
<212> TYPE: PRT
<213> ORGANISM: artificial sequence
<220> FEATURE:
<223> OTHER INFORMATION: pepID 27 MT

<400> SEQUENCE: 22

Lys Val Leu Gln Leu Leu Glu Pro Glu Ile
1               5                   10

<210> SEQ ID NO 23
<211> LENGTH: 8
<212> TYPE: PRT
<213> ORGANISM: artificial sequence
<220> FEATURE:
<223> OTHER INFORMATION: pepID 12 MT

<400> SEQUENCE: 23

Asn Leu Lys Lys Leu Leu Val Phe
```

```
1               5

<210> SEQ ID NO 24
<211> LENGTH: 11
<212> TYPE: PRT
<213> ORGANISM: artificial sequence
<220> FEATURE:
<223> OTHER INFORMATION: pepID 18 MT

<400> SEQUENCE: 24

Ile Cys Phe Leu Ala Leu Glu Cys Leu Ala His
1               5                   10

<210> SEQ ID NO 25
<211> LENGTH: 10
<212> TYPE: PRT
<213> ORGANISM: artificial sequence
<220> FEATURE:
<223> OTHER INFORMATION: pepID 14 WT

<400> SEQUENCE: 25

Ser Leu Ala Leu Glu Cys Leu Ala His Leu
1               5                   10

<210> SEQ ID NO 26
<211> LENGTH: 10
<212> TYPE: PRT
<213> ORGANISM: artificial sequence
<220> FEATURE:
<223> OTHER INFORMATION: pepID 21 WT

<400> SEQUENCE: 26

Gln Leu Leu Glu Pro Gln Ile Ser Phe Leu
1               5                   10

<210> SEQ ID NO 27
<211> LENGTH: 9
<212> TYPE: PRT
<213> ORGANISM: artificial sequence
<220> FEATURE:
<223> OTHER INFORMATION: pepID 41 WT

<400> SEQUENCE: 27

Phe Arg Tyr Ser Ser Ala Leu Lys Val
1               5

<210> SEQ ID NO 28
<211> LENGTH: 10
<212> TYPE: PRT
<213> ORGANISM: artificial sequence
<220> FEATURE:
<223> OTHER INFORMATION: pepID 36 WT

<400> SEQUENCE: 28

Ile Arg Gln Glu Tyr Arg Glu Asp Phe Val
1               5                   10

<210> SEQ ID NO 29
<211> LENGTH: 10
<212> TYPE: PRT
<213> ORGANISM: artificial sequence
<220> FEATURE:
<223> OTHER INFORMATION: pepID 7 WT

<400> SEQUENCE: 29

Val Leu Asp Ile Asn Asp Asn Glu Pro Val
1               5                   10
```

<210> SEQ ID NO 30
<211> LENGTH: 10
<212> TYPE: PRT
<213> ORGANISM: artificial sequence
<220> FEATURE:
<223> OTHER INFORMATION: pepID 43 WT

<400> SEQUENCE: 30

Tyr Gln Tyr Ser Ser Pro Ala Leu Pro Thr
1               5                   10

<210> SEQ ID NO 31
<211> LENGTH: 9
<212> TYPE: PRT
<213> ORGANISM: artificial sequence
<220> FEATURE:
<223> OTHER INFORMATION: pepID 30 WT

<400> SEQUENCE: 31

Ala Leu Tyr Pro Phe Glu Ser Arg Ser
1               5

<210> SEQ ID NO 32
<211> LENGTH: 9
<212> TYPE: PRT
<213> ORGANISM: artificial sequence
<220> FEATURE:
<223> OTHER INFORMATION: pepID 33 WT

<400> SEQUENCE: 32

Asn Ile Ser Ser His Ile His Thr Val
1               5

<210> SEQ ID NO 33
<211> LENGTH: 9
<212> TYPE: PRT
<213> ORGANISM: artificial sequence
<220> FEATURE:
<223> OTHER INFORMATION: pepID 42 WT

<400> SEQUENCE: 33

Lys Thr Phe Arg Tyr Ser Ser Ala Leu
1               5

<210> SEQ ID NO 34
<211> LENGTH: 10
<212> TYPE: PRT
<213> ORGANISM: artificial sequence
<220> FEATURE:
<223> OTHER INFORMATION: pepID 27 WT

<400> SEQUENCE: 34

Lys Val Leu Gln Leu Leu Glu Pro Gln Ile
1               5                   10

<210> SEQ ID NO 35
<211> LENGTH: 8
<212> TYPE: PRT
<213> ORGANISM: artificial sequence
<220> FEATURE:
<223> OTHER INFORMATION: pepID 12 WT

<400> SEQUENCE: 35

Asn Leu Glu Lys Leu Leu Val Phe
1               5

```
<210> SEQ ID NO 36
<211> LENGTH: 11
<212> TYPE: PRT
<213> ORGANISM: artificial sequence
<220> FEATURE:
<223> OTHER INFORMATION: pepID 18 WT

<400> SEQUENCE: 36

Ile Cys Ser Leu Ala Leu Glu Cys Leu Ala His
1               5                   10
```

MONITORING AND DIAGNOSIS FOR IMMUNOTHERAPY, AND DESIGN FOR THERAPEUTIC AGENT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790132_402USPC_SEQUENCE_LISTING.txt. The text file is 7.4 KB, was created on Sep. 13, 2018, and is being submitted electronically via EFS-Web.

TECHNICAL FIELD

The present invention relates to monitoring or diagnosis for immunotherapy and designing of a therapeutic agent. More specifically, the present invention relates to a method of analyzing an epitope based on information on the genome (e.g., exosome) and mRNA, information on MHC, and other biological information to design a peptide that is useful in immunotherapy based on the result thereof.

BACKGROUND ART

The recent development in medicine and biology, especially the rapid advancement in next generation sequencers (NGS), has made complete genome analysis of cancer cells relatively easy and has enabled analysis of cellular oncogenic transformation-associated genetic change at the individual level. With such development, individualized therapy using a molecule targeting therapeutic agent for regulating the function of a mutant gene has become common in the field of clinical medicine. Meanwhile, specific cancer immunotherapy targeting mutant gene products (neoantigens) has not been sufficiently studied (Non Patent Literature 1).

Analysis based on a comprehensive database of mutants, which is also called mutanome analysis, has been performed on mutant genes. The objective of mutanome analysis is to develop a method of constructing a database of sequence/structure/function and analyzing the database to predict the structure/function of a protein only from sequence information by comprehensively introducing various amino acid substitution mutations into proteins and measuring the structure and function of each mutant (Non Patent Literature 2).

CITATION LIST

Non Patent Literature

[NPL 1] Schumacher T N, et al., (2015) Science, 348 (6230), 69-74, doi: 10.1126/science.aaa4971, PMID: 25838375

[NPL 2] Castle J C, et al., (2012) Cancer Res., 72(5), 1081-1089, doi: 10.1158/0008-5472.CAN-11-3722. Epub 2012 Jan. 11., PMID: 22237626

SUMMARY OF INVENTION

Solution to Problem

The inventors have developed a method for producing a peptide for treating, monitoring, or diagnosing a disease in a subject as a result of diligent research. This is achieved by obtaining information related to a genome read (e.g., exosome read) of a subject and a mutation thereof, and optionally information on the RNA sequence of the subject and information on the MHC type of the subject, and analyzing an epitope associated with the mutation based on the information related to the genome read (e.g., exosome read) and the mutation thereof, the optional RNA sequence information, the information on the MHC type, and information on the disease, and optionally producing a peptide based on information on the epitope.

Therefore the present invention provides, for example, the following items.

(1) A method of producing a peptide for treating, monitoring, or diagnosing a disease in a subject, the method comprising the steps of:

A) inputting into an analyzer information related to a mutation specific to a diseased tissue of the subject and information on an MHC type of the subject;

B) making the analyzer analyze an epitope associated with the mutation based on the information related to the mutation specific to the diseased tissue, the information on the MHC type, and information on the disease; and C) producing the peptide based on information on the epitope.

(2) The method of the preceding item, wherein the step B) comprises the step of making the analyzer add an annotation for the mutation specific to the disease tissue based on a reference information database to identify a candidate mutation, wherein nucleic acid information of the candidate mutation is then converted to amino acid information to produce a wild-type (WT) peptide and a mutant (MT) peptide, and then the analyzer is made to search for an epitope using the MHC type, the WT peptide, and the MT peptide after which epitopes are ranked, and to output an epitope list.

(3) The method of any one of the preceding items, comprising deriving the mutation specific to the diseased tissue based on the information related to the genome read of the subject and the mutation thereof.

(4) The method of any one of the preceding items, wherein the genome read comprises an exome read.

(5) The method of any one of the preceding items, wherein the information related to the genome read and the mutation thereof is obtained from a normal sample of the subject and a sample with the disease of the subject, respectively, and after the information related to the genome read and the mutation thereof is mapped, the mutation specific to the diseased tissue is searched to identify the mutation specific to the diseased tissue.

(6) The method of any one of the preceding items, wherein the step A) further comprises inputting information on an RNA read of the subject into the analyzer, and the step B) comprises making the analyzer analyze an epitope associated with the mutation based on the information on the RNA read.

(7) The method of any one of the preceding items, wherein the RNA read comprises an RNA read of a diseased tissue, and the method further comprises the step of mapping the RNA read of the diseased tissue for searching for a mutation and/or deriving an amount of expression.

(8) The method of any one of the preceding items, wherein the information on the RNA read comprises an RNA read of a normal tissue, and the method further comprises the step of mapping the RNA read of the normal tissue for searching for a somatic cell mutation and/or deriving an amount of expression, and comparing said amount with the amount of expression derived based on the RNA read of the diseased tissue.

(9) The method of any one of the preceding items, wherein the MHC type is derived from a genome read of the subject.

(10) The method of any one of the preceding items, wherein the step B) comprises at least one step selected from the steps of:

B-1) making the analyzer, based on an existing database, add an annotation and perform a nucleic acid-amino acid conversion on the mutation specific to the diseased tissue to derive information on a wild-type peptide and a disease specific mutant peptide;

B-2) making the analyzer search for an epitope specific to the disease using a known database by using the MHC type, the wild-type peptide, and the disease specific mutant peptide; and B-3) making the analyzer calculate a score from a peptide sequence of an obtained epitope, MHC information (genotype and affinity), and mutation information (chromosome, position, mutation pattern (wild-type/mutant), reliability, priority, and corresponding gene (gene name and amount of expression)) for ranking epitopes to be prioritized, and the step C) comprises the step of:

C-1) producing a peptide based on the ranking.

11) The method of any one of the preceding items, wherein the information related to the genome read and the mutation thereof is obtained from the same subject.

(12) The method of any one of the preceding items, wherein the information related to the genome read and the mutation thereof is obtained from different subjects.

(13) The method of any one of the preceding items, wherein the information related to the genome read and the mutation thereof is obtained from a normal tissue and a tissue with the disease.

(14) The method of any one of the preceding items, wherein the genome read is mapped using bwa, bowtie, novoalign, or a combination thereof.

(15) The method of any one of the preceding items, wherein a mutation of the genome read is searched using a mutation searching program comprising MuTect, VarScan, lofreq, or a combination thereof.

(16) The method of any one of the preceding items, wherein the annotation is added using a program selected from the group consisting of ANNOVAR and snpEff using a gene structure database selected from refGene and ensEmbl and/or a database of known mutation information selected from the group consisting of dbSNP, cosmic, 1000 genomes, and whole exome features.

(17) The method of any one of the preceding items, wherein the RNA read is mapped using a program selected from the group consisting of TopHat and STAR.

(18) The method of any one of the preceding items, wherein the searching for a mutation of RNA is performed using a mutation searching program selected from the group consisting of MuTect, VarScan, GATK, and samtools.

(19) The method of any one of the preceding items, wherein the deriving of an amount of expression of RNA is preformed using a mutation searching program selected from the group consisting of CuffLinks and Erange.

(20) The method of any one of the preceding items, wherein the MHC typing is performed using software selected from the group consisting of HLAminer, Athlates, Sting HLA, HLA caller, OptiType, and omixon.

(21) The method of any one of the preceding items, wherein the subject is a human, and the MHC is HLA.

(22) The method of any one of the preceding items, wherein the search for an epitope is performed using an epitope searching program selected from the group consisting of NetMHCpan, NetHMC, NetMHCcons, and PickPocket.

(23) The method of any one of the preceding items, wherein the ranking is performed by taking into consideration at least one element selected from the group consisting of prioritization of the mutation, presence/absence of gene expression, and prioritization of a peptide.

(24) The method of any one of the preceding items, wherein the prioritization of the mutation takes into consideration at least one element selected from the group consisting of whether the number of mutation searching programs which have found a hit is high or low and the presence/absence of evidence of a mutation at an RNA level.

(25) The method of any one of the preceding items, wherein the presence/absence of gene expression is determined by whether a value of fpkm or rpkm calculated by mapping the RNA read is positive.

(26) The method of any one of the preceding items, wherein the prioritization of the peptide takes into consideration at least one element selected from the group consisting of whether the number of epitope searching programs which have found a hit is high or low, whether the number of mutation searching software which have found a hit is high or low, and a value of IC50<500 nM between HLA-peptide.

(27) The method of any one of the preceding items, wherein the ranking is sorted by applying, in order, a value of IC50 between HLA-peptide, the number of epitope searching programs which have found a hit, and the number of mutation searching softwares which have found a hit.

(28) The method of any one of the preceding items, wherein the disease is tumor or an autoimmune disease.

(29) The method of any one of the preceding items, wherein the step A) comprises at least one step selected from the group consisting of the steps of:

A-1) making the analyzer sequence a genome of the subject to obtain and map the information related to the genome read of the subject and the mutation thereof, and then search for the mutation specific to the diseased tissue to obtain the mutation specific to the diseased tissue;

A-2) making the analyzer sequence an RNA of the subject to obtain information on an RNA read of the subject, map an RNA read of the diseased tissue, and search for a mutation, and/or derive an amount of expression, and optionally map an RNA read of a normal tissue to search for a somatic cell mutation and/or derive an amount of expression to compare said amount with the amount of expression derived based on the RNA read of the disease tissue; and A-3) optionally making the analyzer perform MHC typing of the subject using the genome read of the subject to obtain information on the MHC type of the subject.

(30) A method of identifying a peptide for treating, monitoring, or diagnosing a disease in a subject, comprising the steps of:

A) inputting into an analyzer information related to a mutation specific to a diseased tissue of the subject and information on an MHC type of the subject; and
B) making the analyzer analyze an epitope associated with the mutation based on the information related to the mutation specific to the diseased tissue, the information on the MHC type, and information on the disease.

(31) The method of any one of the preceding items, further having a feature of any one or more of the preceding items.

(32) An apparatus for producing a peptide for treating, monitoring, or diagnosing a disease in a subject, the apparatus comprising:
A) an information inputting unit for inputting information related to a mutation specific to a diseased tissue of the subject and optionally information on an RNA read of the subject and information on an MHC type of the subject;
B) an epitope analyzing unit for analyzing an epitope associated with the mutation based on the information related to the mutation specific to the diseased tissue of the subject and optionally the mRNA sequence information, the information on the MHC type, and information on the disease; and
C) a peptide producing unit for producing a peptide based on information on the epitope.

(33) The apparatus of the preceding item, wherein a procedure defined in any one or more of the preceding items is performed in the unit B.

(34) The apparatus of any one of the preceding items, wherein the unit A comprises at least one of means for sequencing a genome of the subject, means for determining the mutation specific to the diseased tissue of the subject, means for sequencing an RNA of the subject, and means for MHC typing the subject.

(35) An apparatus for identifying a peptide for treating, monitoring, or diagnosing a disease in a subject, comprising:
A) an information inputting unit for inputting information related to a mutation specific to a diseased tissue of the subject and optionally information on an RNA read of the subject and information on an MHC type of the subject; and
B) an epitope analyzing unit for analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease.

(36) The apparatus of any one of the preceding items, wherein a procedure defined in any one or more of the preceding items is performed in the unit B.

(37) The apparatus of any one of the preceding items, wherein the unit A comprises at least one of means for sequencing a genome of the subject, means for determining the mutation specific to the diseased tissue of the subject, means for sequencing an RNA of the subject, and means for MHC typing the subject.

(38) A program for making a computer execute a method of identifying a peptide for treating, monitoring, or diagnosing a disease in a subject, the method comprising the steps of:
A) inputting information related to a mutation specific to a diseased tissue of the subject and optionally information on an RNA read of the subject and information on an MHC type of the subject; and
B) analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease.

(39) The program of the preceding item, further having a feature in any one or more of the preceding items.

(40) A computer readable recording medium storing a program for making a computer execute a method of identifying a peptide for treating, monitoring, or diagnosing a disease in a subject, the method comprising the steps of:
A) inputting information related to a mutation specific to a diseased tissue of the subject and optionally information on an RNA read of the subject and information on an MHC type of the subject; and
B) analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease.

(41) The recording medium of the preceding item, further having a feature in any one or more of the preceding items.

The present invention is intended so that one or more of the above features can be provided not only as the explicitly disclosed combinations, but also as other combinations thereof. Additional embodiments and advantages of the present invention are recognized by those skilled in the art by reading and understanding the following detailed explanation, as needed.

Advantageous Effects of Invention

A more effective immunotherapy or immunological monitoring for various diseases such as cancer and the like is obtained with the present invention.

BRIEF DESCRIPTION OF DRAWINGS

FIG. 3 shows a start screen in the analysis flow, where an exome from tumor, exome from normal tissue, RNA sequence from tumor, and RNA sequence from normal tissue, number of threads, read trimming conditions, trimming of low quality (LQ) region, analysis conditions, and the like can be selected. For example, the type of algorithm such as mapping algorithm and the conditions thereof can be selected and set for analysis conditions.
FIG. 4 shows an analysis condition setting screen. Conditions for exome mapping and mutation search, RNA mapping and expression analysis thereof, mutation detection, annotation for mutations, HLA typing, and software and conditions used for epitope prediction (determination) can be selected and set.

FIG. 6 shows the results of an experiment in Example 1. The Figure shows, from the left, the results of ELISPOT assay on interferon γ (sample No. 14, 33, 41) and intracellular interferon γ staining in this order.

DESCRIPTION OF EMBODIMENTS

Figure 1:
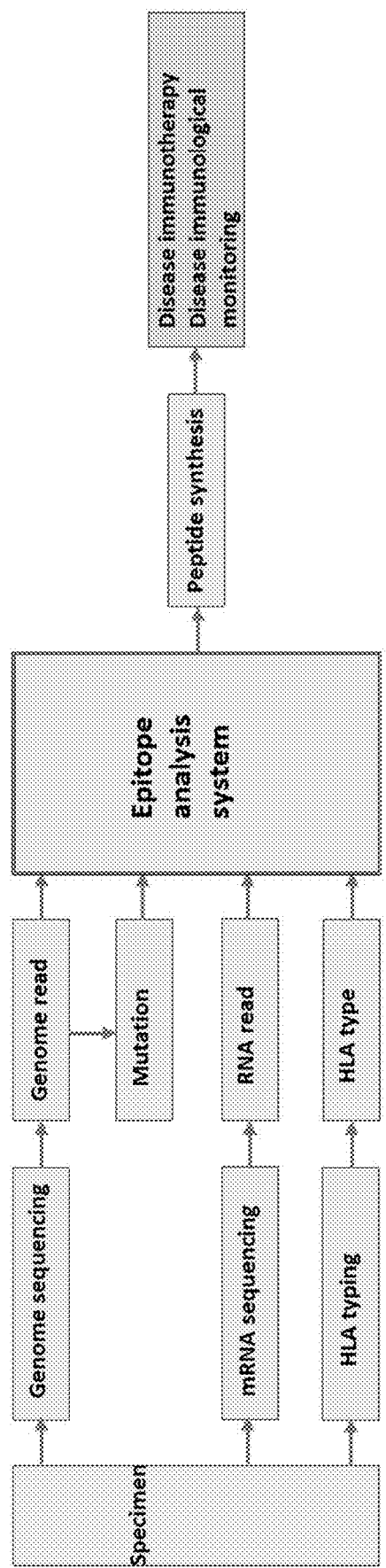
FIG. 1 depicts the concept of the present invention.

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

As used herein, "genome" is used in the meaning that is commonly used in the art, referring to a collection of all chromosomes of an organism.

As used herein, "exome" is used in the meaning that is commonly used in the art, indicating comprehensive analysis of an exon of a genome and comprehensively analyzed exon of a genome. Therefore, an exome is related to comprehensive analysis of anything falling under a part of a genome.

As used herein, "genome read" and "exome read" refer to what is read out (read) from a nucleic acid sequence of a genome and an exome, respectively. A read is generally specified by sequence information based on residues of a base sequence (adenine, cytosine, guanine, and thymine (for DNA) and uracil (for RNA)).

As used herein, "mRNA" is an abbreviation of messenger RNA. MRNA is used in the meaning that is commonly used in the art, referring to an RNA with a structure and base sequence information that can be translated into a protein.

As used herein, "RNA read" refers to what is read out (read) from a nucleic acid sequence for an mRNA. An RNA read is generally specified by sequence information.

As used herein, "mapping" refers to mechanically matching or assigning individual components of a population to components of another population in accordance with a rule. As used herein, "genome mapping" refers to identification of a position on a genome or a chromosome of a nucleic acid sequence or a gene. Further, "mRNA mapping" refers to mapping of mRNA reads onto a genome. Positions where a large quantity of reads is mapped and positions where there is no mapping are alternatingly repeated, which can be analyzed as falling under exons and introns, respectively. mRNA mapping can not only search for a mutation, but also derive the amount of expression by calculating the frequency.

As used herein, "MHC typing" or "HLA typing" refers to identifying of the type of human leukocyte antigens. "MHC" is a major histocompatibility complex, which is human leukocyte antigen (HLA) for humans. MHC type or HLA type can be obtained from an existing database or existing personal information, or can be typed by various approaches. Examples of such a method include serologic testing, sequence-specific oligonucleotide [SSO], sequence-specific primer [SSP], CE sequence based typing [SBT], and the like. Alternatively, when using a next generation sequencing approach such as an approach using Illumina's next generation sequencer, analysis can be performed using the typing method provided therein.

As used herein, "database" refers to any database related to genes. Especially in the present invention, a database comprising information related to mutations of a disease can be used. Examples of such a database include, but are not limited to, the DNA Data Bank of Japan (DDBJ, www.ddbj.nig.ac.jp) database, GenBank (National Center for Biotechnology Information, www.ncbi.nlm.nih.gov/genbank/) database, ENA (EMBL (European Molecular Biology Laboratory), www.ebi.ac.uk/ena) database, IMGT (the international ImMunoGeneTics information system, www.imgt.org) database, and the like.

As used herein, "annotation" refers to providing information (metadata) associated with certain data as notes. In the field of bioinformatics, this refers to providing gene-related information or the like relevant to a certain organism (e.g., sequence information) with other information related to the organism (gene function or the like) as relating notes. In the method of the present invention, information can be added for a searched mutation using a reference information database (DB). Examples of information that can be added include, but are not limited to, positions (exon, intron, regulatory region, intergenic region, or the like), whether there is an amino acid mutation, known information related to a mutation (association with a disease, frequency by race or the like), and the like. Examples of databases that can be used include databases of gene structures (refGene, ensEmbl, and the like), databases of known information on mutations (dbSNP, cosmic, 1000 genomes, whole exome features, and the like), and the like. Annotating software such as ANNOVAR, or snpEff can be used. ANNOVAR is typically used, but the software is not limited thereto.

As used herein, "assign" refers to assigning information such as a specific gene name, function, or characteristic region (e.g., domain, binding region, or the like) to a sequence (e.g., nucleic acid sequence, protein sequence, or the like). Specifically, assigning can be accomplished by inputting or linking specific information for a sequence or the like.

As used herein, "nucleic acid-amino acid conversion" (also abbreviated as NN-AA conversion) refers to conversion of information of a nucleic acid sequence to an amino acid sequence based on codon conversion. For a mutation involving a change in an amino acid, peptides before a change (WT) and after a change (MT) can be derived in the present invention. This is a simple character string conversion, which can be accomplished by common programming or is often a function that is a part of standard software.

As used herein, "disease specific peptide" refers to a peptide whose frequency increases (preferably expressed specifically) when a subject is suffering from a disease, relative to a normal subject. When the disease is for example cancer, the disease specific peptide is referred to as a cancer specific peptide and can be used as an anticancer agent.

Individualized immunotherapy targeting an antigen from a gene mutation (neoantigen) has drawn attention in the field. Especially in the field of cancer, conventionally used cancer antigens have low immunogenicity, so that the clinical effect of specific cancer immunotherapy was not necessarily good. In this regard, it is understood that targeting of a mutant gene involved in malignant transformation of cancer (driver mutation) using a neoantigen that efficiently induces antigen specific T cells with high avidity due to being recognized as "non-autologous" from the immune system results in less avoidance from the immune surveillance due to loss of antigens in cancer cells. It is proposed in this regard that identification of T cell antigen epitope of the like from the driver mutation can be an effective therapeutic method (Yamada T, Azuma K, Muta E, Kim J, Sugawara S, Zhang G L, et al. (2013) PLoS ONE 8(11): e78389. doi:10.1371/journal.pone.0078389), and some clinical trials have been conducted. However, this is addressed conventionally by individually identifying peptide sequences of the like, such that sufficient analysis has not been conducted.

As used herein, "subject" refers to the target subjected to diagnosis, therapy, or the like of the present invention.

As used herein, "test sample" or simply "sample" only needs to be a subject (organism), cell, or a substance derived therefrom of interest, which is considered to comprise an element enabling gene expression.

As used herein, "antigen" refers to any substrate that can be specifically bound by an antibody molecule. As used herein, "immunogen" refers to an antigen that can initiate lymphocyte activation which leads to an antigen specific immune response. As used herein, "epitope" or "antigen determinant" refers to a site in an antigen molecule to which an antibody or a lymphocyte receptor binds. A peptide can be produced (e.g., produced by chemical synthesis or microorganisms) using information on epitopes for use in immunotherapy such as cancer immunotherapy or cancer immunological monitoring. For example, such a peptide can be used as an anticancer agent exerting an antitumor effect by using the peptide as a neoantigen.

As used herein, "diagnosis" refers to identifying various parameters associated with a disease, disorder, condition or the like in a subject to determine the current or future state of such a disease, disorder, or condition. The condition in the body can be examined by using the method, apparatus, or system of the present invention. Such information can be used to select and determine various parameters of a formulation, method, or the like for treatment or prevention to be administered, disease, disorder, or condition in a subject or the like. As used herein, "diagnosis" when narrowly defined refers to diagnosis of the current state, but when broadly defined includes "early diagnosis", "predictive diagnosis", "prediagnosis", and the like. Since the diagnostic method of the present invention in principle can utilize what comes out from a body and can be conducted away from a medical practitioner such as a physician, the present invention is industrially useful. In order to clarify that the method can be conducted away from a medical practitioner such as a physician, the term as used herein may be particularly called "assisting" "predictive diagnosis, prediagnosis or diagnosis". As used herein, "monitoring" refers to evaluation of a reaction of a subject to a medicament for immunotherapy or the like when used in relation to immunotherapy or the like on diseases such as cancer immunity. Any approach can be used for monitoring. One representative example thereof uses enzyme-linked immunospot assay (ELISPOT). ELISPOT assays can be used to evaluate the reaction of a subject to or efficacy of a vaccine, medicament, or biological formulation. ELISPOT assay is a cell assay with one of the highest precision in detecting/listing individual cells secreting a specific protein in vitro. This is based on enzyme-linked immunosorbent assay (ELISA) which was first developed for analyzing a specific antibody secreting cell, but is also used for measuring the frequency of cells that generate/secret other effector molecules such as cytokines. ELISPOT assays can detect cytokine secreting cells with a low frequency of up to 1 in several hundreds of thousands, with a precision that is 200 to 400-fold greater depending on the analyzed cytokine/factor, relative to conventional ELISA assays. Since cytokines released in response to antigens can be mapped to a single cell, the T cell responder frequency can be calculated. ELISPOT can also indicate the type of cytokine response which is considered the type of induced immune response.

ELISPOT assays are different from ELISA in terms of targeting cells instead of a solution for measurement, but they have many similarities in other aspects.

The procedure is briefly explained hereinafter. Tested cells are cultured on a well surface coated with specific capturing antibodies. After removing the cells, secreted molecules are detected in the same manner as ELISA. A spot is formed at a position where a secreting cell was located by using a precipitating substrate. Thus, the frequency of secreting cells is measured instead of the concentration of a substance in a solution in ELISPOT assays. Furthermore, the size and color intensity of each spot represent the amount of cytokines secreted from a cell at the position. When the ELISPOT technique is used in analyzing specific immune responses, a phenomenon, in which T cells start producing cytokines as a part of activation process after attacking antigens, is utilized. Since every cell that has the ability to respond to a certain antigen secretes a corresponding cytokine, it can be identified by such a method. Thus, the technique can be used in any cell, but is frequently used in a method of detecting IFN-γ produced in CD8+ T cells, which are immunologically involved with cytotoxic T cells (CTL) in research for infections, cancer, and vaccine development as the main field of use.

As used herein, "therapy" refers to the prevention of amelioration, preferably maintaining of the current condition, more preferably alleviation, and still more preferably elimination of a disease or disorder (e.g., cancer) in case of such a condition, including being able to exert a prophylactic effect or an effect of improving the disease of a patient or one or more symptoms accompanying the disease. Preliminary diagnosis with suitable therapy may be referred to as "companion therapy" and a diagnostic agent therefor as "companion diagnostic agent". As used herein, "treatment (treat)" refers to application of some type of medical care or remedy on a subject with a disease, disorder, or a risk thereof. Treatment, when broadly defined, encompasses "therapy" and "prevention".

As used herein, "therapeutic drug (agent)", when broadly defined, refers to all agents capable of treating a condition of interest (e.g., diseases such as cancer or the like) and refers to an inhibiter (e.g., antibody) such as those provided by the present invention. In one embodiment of the present invention, "therapeutic agent" may be a pharmaceutical composition comprising an active ingredient and one or more pharmacologically acceptable carriers. A pharmaceutical composition can be manufactured, for example, by mixing an active ingredient and the above-described carriers by any method known in the technical field of pharmaceuticals. Further, usage form of a therapeutic agent is not limited as long as it is used for therapy. A therapeutic agent may be an active ingredient alone or a mixture of an active ingredient and any ingredient. The shape of the carriers is also not particularly limited. For example, the carriers may be a solid or liquid (e.g., buffer).

As used herein, "prevention" refers to the action of taking a measure against a disease or disorder (e.g., cancer) from being in such a condition, prior to being in such a condition.

For example, it is possible to use the agent of the present invention to perform diagnosis, and use the agent of the present invention as needed to prevent or take measures to prevent cancer or the like.

As used herein, "prophylactic drug (agent)", when broadly, refers to all agents capable of preventing a condition of interest (e.g., diseases such as cancer or the like).

As used herein, "agent", when broadly defined, may be any substance or other elements (e.g., energy, radiation, heat, electricity and other forms of energy) as long as the intended objective can be achieved. Examples of such a substance include, but are not limited to, protein, polypeptide, oligopeptide, peptide, polynucleotide, oligonucleotide, nucleotide, nucleic acid (including for example DNAs such as cDNA and genomic DNA and RNAs such as mRNA), polysaccharide, oligosaccharide, lipid, organic small molecule (e.g., hormone, ligand, information transmitting substance, organic small molecule, molecule synthesized by combinatorial chemistry, small molecule that can be used as a medicament (e.g., small molecule ligand and the like) and a composite molecule thereof. Typical examples of an agent specific to a polynucleotide include, but are not limited to, a polynucleotide having complementarity with a certain sequence homology (e.g., 70% or greater sequence identity) to a sequence of the polynucleotide, polypeptide such as a transcription factor that binds to a promoter region and the like. Typical examples of an agent specific to a polypeptide include, but are not limited to, an antibody directed specifically to the polypeptide or a derivative or analog thereof (e.g., single strand antibody), a specific ligand or receptor when the polypeptide is a receptor or ligand, a substrate when the polypeptide is an enzyme and the like.

The formulation procedure for a diagnostic drug, therapeutic drug, prophylactic drug or the like that can be used in the present invention as a medicament or the like is known in the art. The procedure is described, for example, in Japanese Pharmacopoeia, the United States Pharmacopeia, pharmacopeia of other countries, or the like. Thus, those skilled in the art can determine the amount to be used without undue experimentation from the descriptions herein.

Explanation of Preferred Embodiments

The preferred embodiments of the present invention are explained hereinafter. It is understood that the embodiments provided hereinafter are provided to better facilitate the understanding of the present invention, so that the scope of the present invention should not be limited by the following descriptions. Thus, it is apparent that those skilled in the art can refer to the descriptions herein to make appropriate modifications within the scope of the present invention. These embodiments can be appropriately combined with any embodiment.

(Method of Identifying and Producing an Immunotherapeutic Peptide)

Figure 7:
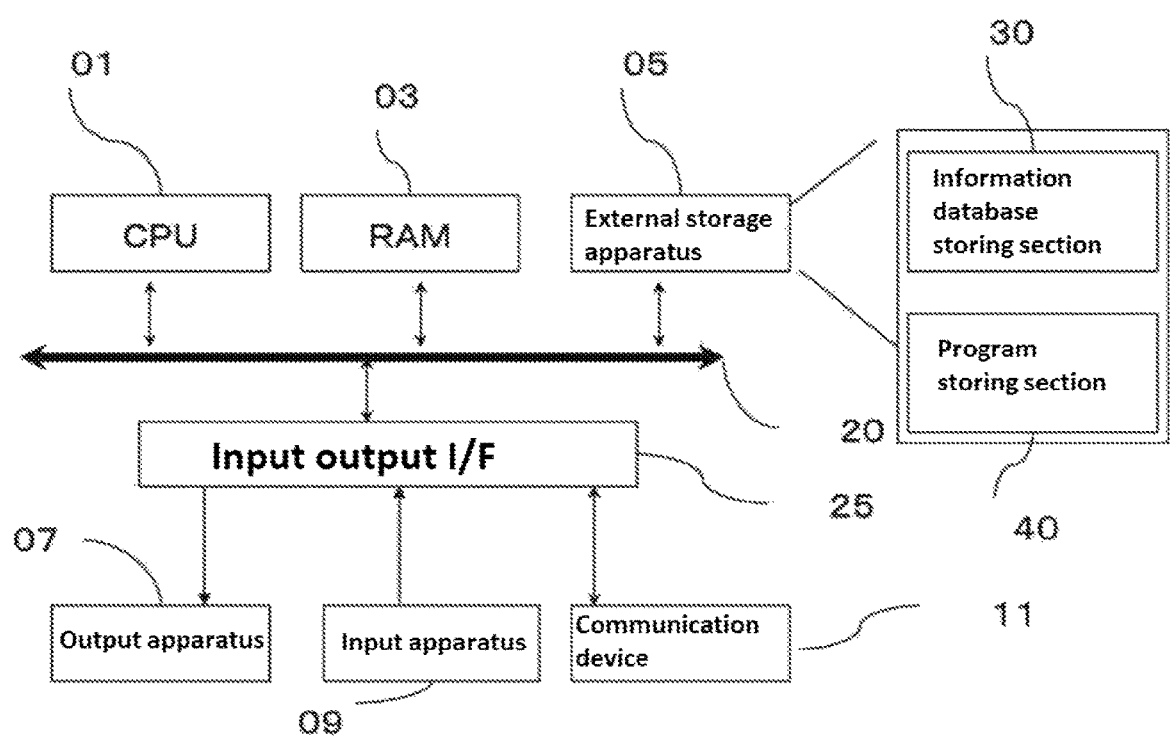
FIG. 7 depicts a block diagram of a system of the present invention.

In one aspect, the present invention provides a method of identifying a peptide for treating (including therapy and prevention), monitoring, or diagnosing a disease in a subject. The method comprising the steps of: A) inputting into an analyzer information related to a mutation specific to a diseased tissue of the subject and information on an MHC type of the subject; B) making the analyzer analyze an epitope associated with the mutation based on the information related to the mutation specific to the diseased tissue, the information on the MHC type, and information on the disease; and C) producing the peptide based on information on the epitope. The "analyzer" used in the present invention can have functions of receiving and analyzing an input of information to be analyzed, making contact with another unit through communication, outputting results or the like. The analyzer is described in detailed in (Immunotherapy analyzer/system and analysis software). Any embodiment therein can be used, and various units can constitute the analyzer. FIG. 7 depicts a schematic diagram of an analyzer, which is described in detail in (System configuration).

In one embodiment, the method of the present invention may comprise the steps of: A) inputting into an analyzer information related to a genome read (e.g., exome read) of the subject and a mutation thereof and optionally information on an RNA sequence of the subject and information on an MHC type of the subject; and B) making the analyzer analyze an epitope associated with the mutation based on the information related to the genome read and the mutation thereof and optionally the information on the RNA sequence, the information on the MHC type, and information on the disease, and output a result thereof as a peptide for treating, monitoring, or diagnosing the disease.

In another aspect, the present invention provides a method of producing a peptide for treating, monitoring, or diagnosing a disease in a subject. The method comprises the steps of: A) inputting into an analyzer information related to a mutation specific to a diseased tissue of the subject and information on an MHC type of the subject; and B) making the analyzer analyze an epitope associated with the mutation based on the information related to the mutation specific to the diseased tissue, the information on the MHC type, and information on the disease.

In one embodiment, the method of the present invention may comprise the steps of: A) inputting into an analyzer information related to a genome read (e.g., exome read) of the subject and a mutation thereof and optionally information on an RNA sequence of the subject and information on an MHC type of the subject; B) making the analyzer analyze an epitope associated with the mutation based on the information related to the genome read and the mutation thereof and optionally the information on the RNA sequence, the information on the MHC type, and information on the disease; and C) producing the peptide based on information on the epitope.

In the method of the present invention, information related to an epitope specific to a disease (e.g., cancer) due to a somatic mutation can be obtained by the analysis, which enables therapy or diagnosis such as immunotherapy or immunological monitoring. Examples thereof include an approach using neoantigens, based on the presence of an immune response targeting an individual gene mutation (unique antigen) so that an antitumor effect is attained, and application, and application thereof to mutanome for comprehensive analysis. Examples of other diseases that can be targeted by the present invention include autoimmune diseases induced by autoreactive T cells. Since T cell abnormality is demonstrated with a basis to be associated with the cause of disease in many autoimmune diseases, such information can be utilized. The present invention can be applied because the invention can identify and isolate specific T cells causing a specific disease and readily determine the recognizing molecule thereof (pathogenic antigen). As for autoreactive T cells, rheumatoid arthritis/type 1 diabetes/multiple sclerosis are diseases caused by specific T cells on unknown antigens in the joint so that they are examples of target diseases. Onset of autoimmune diseases is suppressed by identifying autoantigens recognized by T cells in autoimmunity and suppressing the activation of autoreactive T cells or inhibiting the activation itself. It is fundamentally understood that breakdown of immunological tolerance that is established against itself is associated with the induction of autoimmunity. Meanwhile, the present invention can identify not only known pathogenic antigens (epitope) but also unknown pathogenic antigens to treat or prevent a disease by comprehensively reviewing and searching for the presence/absence of a somatic cell mutation on the antigen side that induces autoimmunity. The present invention can also be applied to diagnosis/prevention of the presence/absence of a pathogenic antigen of an autoimmune disease and to development of a therapeutic drug that targets a pathogenic antigen.

In one embodiment, the step B) performed by the present invention comprises the step of making the analyzer add annotation for the mutation specific to the disease tissue based on a reference information database to identify a candidate mutation, wherein nucleic acid information of the candidate mutation is then converted to amino acid information to produce a wild-type (WT) peptide and a mutant (MT) peptide, and then the analyzer is made to search for an epitope using the MHC type (HLA type for humans), the WT peptide, and the MT peptide after which epitopes are ranked, and to output an epitope list.

In a specific embodiment, the mutation specific to the diseased tissue is derived based on the information related to the genome read of the subject and the mutation thereof.

In one embodiment, the genome read can comprise a genome read from a normal tissue and a genome read from a diseased tissue (e.g., tumor or the like). Therefore, examples of genome reads that can be used in the present invention include reads that are read out from genomic DNA sequence of a diseased tissue (e.g., tumor) or a normal tissue. Examples of methods of obtaining a genome read include, but are not limited to, complete genome sequencing method and exome sequencing method. Therefore, information related to a genome read and a mutation thereof is obtained from a normal sample of the subject and a sample with the disease of the subject, respectively, and after the information related to the genome read and the mutation thereof is mapped, the mutation specific to the diseased tissue is searched to identify the mutation specific to the diseased tissue. Examples of equipment that can be used include, but are not limited, any next generation sequencer (e.g., Illumina, Roche 454, and the like), capillary sequencers, and the like. It is understood that any approach can be used as long as a nucleic acid sequence (gene sequence) can be read. In particular, exome sequences are typically used.

In one embodiment, a genome read utilizing by the present invention comprise an exome read. Exome relates to comprehensive analysis of an exon constituting the main portion of a genome and analyzed results thereof. Although not wishing to be bound by any theory, it is understood that targeting exome reads for investigation can target information with a closer association with an actually functioning protein for investigation, so that the precision of analysis can be improved.

In one embodiment, the method of the present invention utilizes information on an RNA read of a subject. Thus, in a specific embodiment, the step A) further comprises inputting information on an RNA read of the subject into the analyzer, and the step B) comprises making the analyzer analyze an epitope associated with the mutation based on the information on the RNA read. In a specific embodiment, the RNA read comprises an RNA read of a diseased tissue, and the method further comprises the step of mapping the RNA read of the diseased tissue for searching for a mutation and/or deriving an amount of expression. In a preferred embodiment, the information on the RNA read used in the present invention comprises an RNA read of a normal tissue, and the method further comprises the step of mapping the RNA read of the normal tissue for searching for a somatic cell mutation and/or deriving an amount of expression, and comparing said amount with the amount of expression derived based on the RNA read of the diseased tissue. Although not wishing to be bound by any theory, the precision of a hit of a resulting epitope dramatically increases by including and using information on what is read out (read) from a nucleic acid sequence for an RNA read of a subject, i.e., mRNA, thus attaining a hit rate of about 30% (by interferon γ secretion assay as an exemplary example) as demonstrated in the Examples. Therefore, it has been revealed that a markedly significant level of hit rate which was not possible in the past can be achieved. Examples of RNA reads that can be used in the present invention include reads from reading an RNA sequence of a diseased tissue (e.g., tumor) and/or a normal tissue. It is understood that such RNA sequences can be sequenced by, but not limited to, approaches using RNA-Seq with a next generation sequencer, EST analysis with a capillary sequencer, or any approach as long as an RNA sequence can be read. RNA-Seq with a next generation sequencer is the most representative.

Any typing approach can be used as the MHC (HLA) typing that can be practiced in the present invention. For example, typing can be performed using software from a genome read. An assay system for direct typing from a specimen such as the Luminex assay can also be used.

In another specific embodiment, the step B), which is a step for analysis, comprises at least one step selected from the steps of: making the analyzer derive information on a wild-type peptide and a disease specific mutant peptide; making the analyzer search for an epitope specific to the disease; and making the analyzer calculate a score from an obtained epitope for ranking epitopes to be prioritized. In a preferred embodiment, the method comprises the steps of: making an analyzer identify a mutation specific to a disease, and making the analyzer add annotation for the mutation specific to the disease tissue based on a reference information database to identify a candidate mutation, wherein nucleic acid information of the candidate mutation is then converted to amino acid information to produce data of a wild-type (WT) peptide and a mutant (MT) peptide, and then an epitope is searched using the MHC type (HLA type for humans) and the data of the WT peptide and the MT peptide after which epitopes are ranked, and an epitope list is output.

In a preferred embodiment, the method of the present invention has one or more features of at least one step selected from the steps of: B-1) making the analyzer, based on an existing database, add an annotation, and perform a nucleic acid-amino acid conversion on, the mutation specific to the diseased tissue to derive information on a wild-type peptide and a disease specific mutant peptide; B-2) making the analyzer search for an epitope specific to the disease using a known database by using the MHC type, the wild-type peptide, and the disease specific mutant peptide; and B-3) making the analyzer calculate a score from a peptide sequence of an obtained epitope, MHC information (genotype and affinity), and mutation information (chromosome, position, mutation pattern (wild-type/mutant), reliability, priority, and corresponding gene (gene name and amount of expression)) for ranking epitopes to be prioritized.

In a preferred embodiment, the method of the present invention optionally comprises making an analyzer perform at least one of the following steps in addition to B-1) to B-3): obtaining information related to the genome read and the mutation thereof from a normal sample of the subject and a sample with the disease of the subject, respectively, and after the information related to the genome read and the mutation thereof is mapped, the mutation is searched to identify the mutation specific to the diseased tissue; optionally identifying and mapping a sequence specific to the disease from the information on the RNA read for searching for a mutation and/or deriving an amount of expression, and optionally MHC typing from information related to an abnormality specific to the normal tissue and the disease tissue to identify the MHC type.

More specifically, step B) comprises the step of first making the analyzer, based on an existing database, add an annotation and perform a nucleic acid-amino acid conversion on a mutation specific to the diseased tissue to derive information on a wild-type peptide and a disease specific mutant peptide as B-1). For a mutation specific to a disease that is used in this regard, already existing data may be utilized, and the following deriving step may be performed. In the deriving step, information related to the genome read and a mutation thereof is obtained from a normal sample of the subject and a sample with the disease of the subject, respectively, and after the information related to the genome read and the mutation thereof is mapped (aligned), the mutation specific to the diseased tissue is searched to identify the mutation specific to the diseased tissue, and an annotation is added and a nucleic acid-amino acid conversion is performed on the mutation specific to the diseased tissue to derive information on a wild-type peptide and a disease specific mutant peptide. A somatic cell mutation can be searched by analyzing information on these wild-type peptide and disease specific mutant peptide. The deriving step can be considered an additional flow upon inputting a genome read or exome read.

In this regard, genome mapping that can be performed in the present invention refers to mapping of a genome read to a genome sequence. Preferably, cleanup of a read in advance can be advantageous.

The approach for cleaning up a read that can be used in the present invention can use any approach. Representative examples thereof include deletion of a region that is unsuitable for analysis from a genome read (e.g., exome read) and/or RNA read, such as removal of a sequencing adaptor sequence, removal of a low quality region, removal of contaminations, and the like. Removal of contaminations is materialized by not trimming a portion of a read, but by removing an unsuitable read from a read set. For example, a sequence from a bacteria or virus can be removed prior to human genome analysis.

Any approach known in the art can be used as the approach for removing a sequencing adaptor sequence. Representative examples thereof including removing a region found to match an adaptor sequence with a mismatch rate of 10% or less over a suitable length, such as 12 bp or greater (or 10 bp or greater, 11 bp or greater, 13 bp or greater, 14 bp or grater or the like). The mismatch rate can be appropriately changed. For example the mismatch rate can be 1% or less, 2% or less, 3% or less, 4% or less, 5% or less, 10% or less, 15% or less, 20% or less, or the like.

Any approach known in the art can be used for removing a low quality region. Representative examples include removing a region having a mean quality value for a suitable length, such as 10 bp, of a predetermined value such as 12 or less when found from both ends of a read.

As used herein, "mean quality value" refers to a value indicating the quality of analysis in gene analysis software. The value is appropriately set in the software to be used (e.g., sequencing software or the like). The "quality value" used herein is a value quantifying the reliability of each base on a read that is output from various sequencers (defined as $-\log 10(X) \times 10$ where the error rate of the base is X). The error rate of each base varies for each sequencer. The error rate is evaluated as a quality value for each sequencer model by their own logic. Since it is a frontend computer controlling the sequencer and software running thereon that perform the evaluation, the error rate is appropriately set in commonly used software (e.g., sequencing software). In this regard, "mean quality value" is an arithmetic mean value of quality values in a region with a determined length.

The mean length for finding the mean quality value may be a value other than those discussed above. Examples thereof include lengths of 5 bp, 6 bp, 7 bp, 8 bp, 9 bp, 10 bp, 11 bp, 12 bp, 13 bp, 14 bp, 15 bp, and longer. Examples of a mean quality value include 10 or less, 11 or less, 12 or less, 13 or less, 14 or less, 15 or less, and the like.

Examples of software that can be used in genome mapping include bwa, bowtie, novoalign, and the like. Typically, bwa can be used. Bwa and bowtie are published, freely downloadable software. Novoalign is commercially available software that is available to those skilled in the art.

The somatic cell mutation search in the present invention refers to a search for a mutation found in only a diseased tissue (e.g., tumor tissue) from comparing the diseased tissue to a normal tissue. Such a search can also be materialized by software. Examples of software that can be used include mutation searching programs such as muTect, VarScan, and lofreq. Typically, muTect can be used. Such software can be used concurrently. The reliability can be improved by concurrent use of two or more types (2 types, 3 types, or the like) of software.

In the annotation performed in B-1), information can be added using a reference information database for a searched mutation. In this regard, information such as positions (exon, intron, regulatory region, intergenic region, or the like), whether there is an amino acid mutation, or known information related to a mutation (association with a disease, frequency by race or the like) can be added. Examples of databases that can be used include, but are not limited to, refGene, ensEmbl, and the like as databases of gene structures. Examples of known information on mutations include, but are not limited to, dbSNP, cosmic, 1000 genomes, whole exome features, and the like. Examples of software that can be used include, but are not limited to, ANNOVAR, snpEff, and the like. ANNOVAR is preferably used. Databases that can be used further include hg19. Hg19 is a human genome sequence database, which can be used generally as the background as a reference sequence of mapping.

Step B) can also optionally comprise a step of identifying and mapping a sequence specific to the disease from the information on the RNA read for searching for a mutation and/or deriving an amount of expression. The accuracy can be improved by including information on an RNA read.

Mapping of mRNA can be materialized by mapping an RNA read onto a genome sequence while taking into consideration the exon-intron structure. As was the case for genome reads, the reads are cleaned up in advance in some cases. For such a cleanup technique, the same technique as that for genome reads can be used. MRNA mapping can be materialized by software. Examples of software that can be used include TopHat, STAR, and the like. Typically, TopHat is used.

As was the case for genome reads, RNA reads of a normal tissue and diseased tissue (tumor or the like) can be analyzed. mRNA mapping can be performed therefor to search for a mutation. For a mutation search, a somatic cell mutation can be search as was the case for genome reads. In addition, a mutation can be searched in a diseased tissue (e.g., tumor). Such a mutation search in a diseased tissue searches for a mutation found in a single specimen. Representative examples of software that can be used include muTect, VarScan, GATK, samtools, and the like. Typically, GATK can be used.

More characteristically for RNA reads, the amount of expression can be derived and reflected in analysis. Derivation and comparison of the amount of expression can be materialized by converting mRNA mapping results into the amount of expression of each gene. In this regard, analysis can be performed by deeming the quantity of reads mapped to each locus as the amount of expression. The unit is generally, but is not limited to, FPKM or RPKM (Fragments/Reads Per Kilobase of exon per Million mapped reads). The amount of expression can be compared between specimens or the like. Representative examples of software that can be used include CuffLinks, Erange, and other mutation searching programs. Typically, CuffLinks is used, but the software is not limited thereto.

When an RNA read of a diseased tissue is used concurrently, mRNA mapping of the RNA read of the diseased tissue (e.g., tumor tissue), mutation search, and expression amount derivation can be performed, and information on such a mutation and expression amount can be used for prioritizing a list of epitopes.

When an RNA read of a normal tissue is used concurrently, mRNA mapping of the RNA read of the normal tissue, somatic cell mutation search and expression amount derivation can be performed, and such information can be used in prioritizing a list of epitopes. When an RNA read of a diseased tissue is further used concurrently, the information on the difference in the amounts of expression between the diseased tissue and the normal tissue from comparing the amount of expression derived from an RNA read from a diseased tissue and the amount of expression derived from an RNA read of a normal tissue and information on a somatic cell mutation can be used for prioritizing a list of epitopes.

Step B) can also optionally comprise the step of making the analyzer perform MHC typing from information related to an abnormality specific to the normal and diseased tissue to identify an MHC type. In this regard, MHC typing (HLA typing for humans) can determine the HLA type from a genome read, but a result of typing in another assay system can also be used. When software is used, software such as HLAminer, Athlates, Sting HLA, HLA caller, OptiType, omixon, or the like can be used. Typically, omixon (human) or HLA caller (mouse) is used.

Step B) can also comprise the step of B-2) making the analyzer search for an epitope specific to the disease using a known database by using the MHC type, the wild-type peptide, and the disease specific mutant peptide. In this regard, a specific epitope search can search for a partial peptide with affinity for a designated HLA type from designated peptides. Examples of software that can be used include, but are not limited to, NetMHCpan, NetHMC, NetMHCcons, PickPocket, and the like. Preferably, NetMHCpan is used. Concurrent use can improve the reliability. This can also be performed in a mouse, rat, rhesus monkey, chimpanzee, or the like in addition to humans by switching the reference database.

Step B) can also comprise the step of B-3) making the analyzer calculate a score from a peptide sequence of an obtained epitope, MHC information (genotype and affinity), and mutation information (chromosome, position, mutation pattern (wild-type/mutant), reliability, priority, and corresponding gene (gene name and amount of expression)) for ranking epitopes to be prioritized.

Another feature of a preferred embodiment includes searching for partial peptides with affinity in MHC information (HLA information) and then checking whether they comprise an amino acid mutation position and saving only the former to eliminate useless results for improving the efficiency in an analyzer in step B-3). Improved efficiency and/or improved precision in analysis results are achieved thereby.

Examples of a baseline for selecting an epitope include prioritization of mutations, presence/absence of gene expression, prioritization peptides, and the like.

In a preferred embodiment, the baseline of epitope selection includes prioritization of mutations. Examples of prioritization of mutations include, but are not limited to, raising the priority when found in multiple types of mutation searching software and/or there is evidence of being from an RNA read, and the like. Alternatively, raising priority may also be considered when there is gene expression. The presence/absence of gene expression can be determined by whether a value of fpkm or rpkm calculated by mapping an RNA read from the results of the RNA read is positive. It has been revealed that utilization of a result of an RNA read contributes to improved accuracy as shown in the Examples. Alternatively, peptides can be prioritized. In this regard, whether or not a peptide is found by multiple types of epitope searching software can be used for prioritizing peptides. Prioritization of peptides can also be determined by referring to the IC50 levels between HLA-peptide or the like. Examples thereof include, but are not limited to, IC50<500 nM, preferably IC50<400 nM, IC50<300 nM, IC50<200 nM, IC50<100 nM, IC50<90 nM, IC50<80 nM, IC50<70 nM, IC50<60 nM, IC50<50 nM, and the like. Intermediate values thereof (e.g., IC50<54 nM and the like used in the Examples) can also be appropriately changed and used as a threshold value in view of the search results.

In a preferred embodiment, the prioritization of peptides takes into consideration at least one element selected from whether the number of epitope searching programs which have found a hit is high or low, whether the number of mutation searching software which have found a hit is high or low, and a value of IC50<500 nM between HLA-peptide. More preferably, ranking is sorted by applying, in order, a value of IC50 between HLA-peptide, the number of epitope searching programs which have found a hit, and the number of mutation searching softwares which have found a hit. Although not wishing to be bound by any theory, an antigen peptide can be identified with surprisingly high precision by such a sorting method.

In another embodiment, the information related to the genome read and the mutation thereof is obtained from the same subject in the present invention. Analysis can be performed while considering a change in the same person by obtaining information from the same subject. In this regard, the information related to the genome read and the mutation thereof is preferably obtained from a normal tissue and a tissue with the disease.

In another embodiment in the present invention, the information related to the genome read and the mutation thereof is obtained from different subjects. Preferably, a normal subject is included in the different subjects so that a comparison with a subject suspected of having a disease can be clear. These differences can be identified as disease specific mutations (e.g., tumor specific mutation for cancer) by genome mapping and then searching for a somatic cell mutation.

Once a disease specific mutation is obtained in this manner, an analyzer can be made to add an annotation using an appropriate reference information database (DB), identify a candidate mutation, and convert the information thereof into amino acid information. A wild-type peptide and a mutant peptide can be generated based on a candidate amino acid sequence converted in this manner.

Annotation as used herein refers to addition of information for a searched mutation using a reference information DB. Examples of information that can be added include, but are not limited to, positions (exon, intron, regulatory region, intergenic region, and the like), whether there is an amino acid mutation, known information related to a mutation (association with a disease, frequency by race and the like), and the like. Examples of databases that can be used in annotation include refGene, ensEmbl, and the like for investigating gene structures. For known information on mutations, dbSNP, cosmic, 1000 genomes, whole exome features, and the like can be used. ANNOVAR, snpEff, and the like can be used as a whole, while ANNOVAR is typically used, but the database is not limited thereto.

In the method of the present invention, nucleic acid-amino acid conversion (NA-AA conversion) is performed, which is materialized by converting a common codon code. There is no need to use special software because this is accomplished by simple character string conversion. For a mutation involving a change in amino acid, peptides before a change (WT) and after a change (MT) can be derived in the present invention, after the conversion into an amino acid. A mutation that does not change at the amino acid level can be removed thereby.

Next, an epitope can be searched by comparison to information on HLA types based on wild-type and mutant peptides. An epitope search can search for a partial peptide with affinity for a designated HLA type from designated peptides. Examples of software that can be used include, but are not limited to, NetMHCpan, NetHMC, NetMHCcons, PickPocket, and the like. Typically, NetMHCpan is used. Concurrent use of two or more types of software can improve the reliability. Furthermore, this can be typically materialized using a database for mammals such as humans, primates, or rodents, but this can be materialized for a mouse, rat, rhesus monkey, chimpanzee, or the like by switching a reference database in place of the exemplary human examples that have been run.

When a peptide is produced in the method of the present invention, peptide sequence information is provided, so that a peptide can be produced by any production method that can be practiced based on the sequence information, such as chemical synthesis, product with microorganisms, or cleavage of a larger peptide (e.g., enzymatic cleavage). Peptide synthesis (chemical synthesis) is preferred. These are preferred synthesis methods with respect to large-scale production and/or precision.

The present invention can also be practiced in animals by the same approach as that for humans. The examples thereof are described below.

1. Neoantigens can be searched in spontaneously, chemically, and radiation induced tumor (cancer, sarcoma, or leukemia) in mouse of all strains (syngenic).
2. Tissue is collected from a cancerous site in a cancer bearing mouse, and the same organ/tissue as the tumor site is collected in a normal mouse, where a tumor site and non-tumor site (e.g., tumor site and non-tumor site for colon cancer) are collected in the cancer bearing mouse. When the mice are from the same strain, normal tissue can be collected from the normal mouse.
3. DNA and RNA are extracted from the collected tissue/organ to perform exome seq and RNA seq analysis.
4. Since the MHC (major histocompatibility complex) is known for each strain, the mutanome that can be used in the present invention is searched, and then neoantigens presented on the MHC (H-2 in mice) are identified.
5. For selection of neoantigens, the same methodology as that described for human tumor exemplified in the Examples can be used.
6. For the identified neoantigens, a peptide can be artificially synthesized, and added and cultured in spleen cells of syngenic mouse to use induction of IFNγ production after culturing as an indicator of activation.
7. The spleen cells that has been stimulated with neoantigens and cultured are used to measure cytotoxicity to tumor.
8. The following is performed if it is clear that searched neoantigens functionally induce T cells against tumor from studying the content of a test tube.
9. In other words, the in vivo effect using the candidate neoantigens is examined.
10. As the in vivo effect, neoantigens are directly administered to a cancer bearing mouse (mouse to which tumor used in neoantigen search is transplanted). Further, dendritic cell therapy (dendritic cells from syngenic mice are stimulated and cultured in vitro and administered to the cancer bearing mice) can be used for therapy.

(Immunotherapy Analyzer/System and Analysis Program)

In another aspect, the present invention provides an apparatus or system for producing a peptide for treating, monitoring, or diagnosing a disease in a subject. the apparatus or system comprises: A) an information inputting unit for inputting information related to a mutation specific to a diseased tissue of the subject and optionally information on an RNA read of the subject and information on an MHC type of the subject; B) an epitope analyzing unit for analyzing an epitope associated with the mutation based on the information related to the mutation specific to the diseased tissue of the subject and optionally the mRNA sequence information, the information on the MHC type, and information on the disease; and C) a peptide producing unit for producing a peptide based on information on the epitope. The information inputting unit, analyzing unit, and synthesis unit used in this regard can comprise any of the features explained in (Method of identifying and producing an immunotherapeutic peptide). The "analyzer" used in the present invention can comprise an information inputting unit and an epitope analyzing unit. The analyzer of the present invention may also comprise at least one additional unit having another function. These units are explained below.

In another aspect, an apparatus or system for identifying a peptide for treating, monitoring, or diagnosing a disease in a subject. The apparatus or system comprises A) an information inputting unit for inputting information related to a mutation specific to a diseased tissue of the subject and optionally information on an RNA read of the subject and information on an MHC type of the subject; and B) an epitope analyzing unit for analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease. The information inputting unit and the analyzing unit used herein can comprise any of the features explained in (Method of identifying and producing an immunotherapeutic peptide).

In yet another aspect, the present invention provides a program for making a computer execute a method of identifying a peptide for treating, monitoring, or diagnosing a disease in a subject. The method executed by the program comprises the steps of: A) inputting information related to a mutation specific to a diseased tissue of the subject and optionally information on an RNA read of the subject and information on an MHC type of the subject; and B) analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease. The program may be stored in a recording medium and transmitted by a transmission medium. The method executed in this regard can comprise any of the features explained in (Method of identifying and producing an immunotherapeutic peptide).

Thus, the present invention provides a recording medium storing a program for making a computer execute a method of identifying a peptide for treating, monitoring, or diagnosing a disease in a subject. The method executed by a program stored therein comprises the steps of: A) inputting information related to a mutation specific to a diseased tissue of the subject and optionally information on an RNA read of the subject and information on an MHC type of the subject; and B) analyzing an epitope associated with the mutation based on the information related to the mutation specific to the diseased tissue of the subject and optionally the mRNA sequence information, the information on the MHC type, and information on the disease, and outputting a result thereof as a peptide for treating, monitoring, or diagnosing the disease. The recording medium can be a RAM, ROM, or an external storage apparatus such as a hard disk (HDD), magnetic disk (DVD or the like), or a flash memory such as USB memory. The method executed in this regard can comprise any of the features explained in (Method of identifying and producing an immunotherapeutic peptide).

For example, in one embodiment, unit A (information inputting unit) can comprise at least one of means for sequencing a genome of a subject, means for sequencing an RNA of the subject, and means for MHC typing the subject. Further, step A) executed by a program comprises at least one step selected from the group consisting of the steps of: A-1) sequencing a genome of the subject to obtain and map the information related to the genome read of the subject and the mutation thereof, and then searching for the mutation specific to the diseased tissue to obtain the mutation specific to the diseased tissue; A-2) sequencing an RNA of the subject to obtain information on an RNA of the subject, mapping an RNA read of the diseased tissue, and searching for a mutation, and/or deriving an amount of expression, and optionally mapping an RNA read of a normal tissue to search for a somatic cell mutation and/or deriving an amount of expression to compare said amount with the amount of expression derived based on the RNA read of the disease tissue; and A-3) optionally performing MHC typing of the subject using the genome read of the subject to obtain information on the MHC type of the subject.

Unit B (analyzing unit) can have various functions. Further, step B) executed by the program executes various functions. The step performed by the analyzing unit or the analyzing step can comprise any step for implementing an action for materializing the concept depicted in FIG. 1 on a computer and additionally any step for implementing an action for materializing any step of the analysis flow depicted in FIG. 2 on a computer.

In particular, unit B or step B) executed by a program preferably implements a step of inputting or identifying a mutation specific to a diseased tissue and a step of adding an annotation for a mutation specific to a disease based on a reference information database to identify a candidate mutation, wherein nucleic acid information of the candidate mutation is then converted to amino acid information to produce a wild-type (WT) peptide and a mutant (MT) peptide, and then an epitope is searched for using the MHC type (HLA type for humans), the WT peptide, and the MT peptide, after which epitopes are ranked, and an epitope list is outputted.

For a mutation specific to a disease, already existing data can be used or a system can be B-1) made to perform the step of adding an annotation based on an existing database and performing nucleic acid-amino acid conversion on the mutation specific to a diseased tissue to derive information on a wild-type peptide and a disease specific mutant peptide. The program of the present invention performs such a step. The details of step B-1) are explained in (Method of identifying and producing an immunotherapeutic peptide).

Preferably, a mutation specific to a diseased tissue is derived based on information related to a genome read of a subject and a mutation thereof. In this regard, the information related to the genome read and the mutation thereof is obtained from a normal sample of the subject and a sample with the disease of the subject, respectively, and after the information related to the genome read and the mutation thereof is mapped, the mutation specific to the diseased tissue is searched to identify the mutation specific to the diseased tissue.

Preferably, analysis of information on an RNA read may be implemented by the apparatus or system of the present invention. In such a case, a step of identifying and mapping a sequence specific to the disease from the information on the RNA read for searching for a mutation and/or deriving an amount of expression can be optionally implemented by the apparatus or system of the present invention. Such a step can be performed in the program of the present invention. The accuracy can be improved by including information on an RNA read. The details of the step of obtaining information on an RNA read are explained in (Method of identifying and producing an immunotherapeutic peptide).

In the apparatus or system of the present invention, known information can be used as the MHC type (or HLA type) or a step of identifying the MHC type can be implemented. Thus, the apparatus or system of the present invention can optionally implement a step of performing MHC typing from information related to an abnormality specific to the normal and diseased tissue to identify an MHC type. Such a step can be implemented by the program of the present invention. The details of MHC type identifying step are explained in (Method of identifying and producing an immunotherapeutic peptide).

In the apparatus or system of the present invention, a step of B-2) searching for an epitope specific to the disease using a known database by using the MHC type, the wild-type peptide, and the disease specific mutant peptide can be implemented. Such a step can be implemented by the program of the present invention. An epitope is searched thereby. The details of step B-2) are explained in (Method of identifying and producing an immunotherapeutic peptide).

In the apparatus or system of the present invention, a step of ranking epitopes can be implemented. Such a step is performed by the program of the present invention. Thus, a step of B-3) calculating a score from a peptide sequence of an obtained epitope, MHC information (genotype and affinity), and mutation information (chromosome, position, mutation pattern (wild-type/mutant), reliability, priority, and corresponding gene (gene name and amount of expression)) for ranking epitopes to be prioritized can be implemented by the apparatus or system of the present invention. Such a step can be performed by the program of the present invention. The details of step B-3) are explained in (Method of identifying and producing an immunotherapeutic peptide).

When the apparatus or system of the present invention produces a peptide, the apparatus or system may comprise a peptide producing unit for producing the peptide based on information on an epitope. Since such a peptide producing unit is provided with peptide sequence information, the apparatus or system can comprise any unit that materializes the product by any production method that can be practiced based on the sequence information, such as chemical synthesis, production with microorganisms, or cleavage of a larger peptide (e.g., enzymatic cleavage).

The program of the present invention can be combined with a program performing the production of a peptide. Alternatively, a program materializing the step of executing production of a peptide can be incorporated as a part of the program of the present invention.

(System Configuration)

Next, the configuration of the system or apparatus of the present invention is explained while referring to the block diagram in FIG. 7. This diagram depicts a case materialized with a single system, but the system or apparatus may be composed of multiple units or components.

The system of the present invention is comprised of a RAM 03, ROM, and an external storage apparatus 05 such as an HDD, magnetic disk, or a flash memory such as USB memory, and an input/output interface (I/F) 25 connected to a CPU 01 that is built into a computer system via a system bus 20. The input/output I/F 25 is connected to each of an input apparatus 09 such as a keyboard or a mouse, an output apparatus 07 such as a display, and a communication device 11 such as a modem. The external storage apparatus 05 comprises an information database storing section 30 and a program storing section 40. They are both a constant storage region reserved inside the external storage apparatus 05.

In such a hardware configuration, a software program installed in the storing apparatus 05 is called by the CPU 01 onto the RAM 03, deployed, and executed by an input of various instructions (command) via the input apparatus 09 or by receiving a command via the communication I/F, communication device 11 or the like to achieve the function of the invention in cooperation with an OS (operating system).

The database storing section 30 is confirmed to have a reference database, input sequence set, generated genome read data, RNA read data, MHC (HLA) type data, data such as specific mutation data, software executing various steps, and a database in some cases. Alternatively, information obtained via the communication device 11 or the like is continuously written and updated. Optionally, information attributed to a sample subjected to accumulation can be managed with an ID defined in each master table by managing each sequence in each input sequence set, each gene information ID of a reference database and other information in each master table.

Information (including IDs and the like) related to a subject of a normal tissue or diseased tissue (e.g., cancer tissue), information on samples, information on sequence analysis (read), information related to various mutations, information on mapping, information on annotation, information on nucleic acid-amino acid conversion, information on amount of expression, information on comparison thereof, information on wild-type, mutant type, and MHC (HLA) type and the like are stored while being associated with a sample ID as input entry information in the database storing section 30. In this regard, analysis result is information obtained by processing of the present invention.

The computer program stored in the program storing section 40 configures a computer as the program of the present invention or the apparatus or system of the present invention comprising processing such as epitope search or epitope prioritization. These functions are each independently a computer program or a module or routine thereof, which configures a computer as each of the system or apparatus by being executed by the CPU 01.

General Techniques

Molecular biological methodology, biochemical methodology, and microbiological methodology used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, or the like. Relevant portions (which may be all) thereof are incorporated herein by reference.

Examples of documents showing conventional common general knowledge in bioinformatics include Gibas C. et al.

(2001). Developing Bioinformatics Computer Skills, O'Reilly; Mount D. W., (2004). Bioinformatics: Sequence and Genome Analysis, CSHL Press; Pevzner P. et al. (2011). Bioinformatics for Biologist, Cambridge University Press; SUGENO, Sumio et al. (2012) Saibokogaku Bessatsu [*Cell Engineering, Supplemental Volume*] "Jisedai Shikuensa Mokutekibetsu Adobansuto Mesoddo" [Next Generation Sequencer, Advanced Method by Objective], Shujunsha. Relevant portions (which may be all) thereof are incorporated herein by reference.

Reference literatures such as scientific literatures, patents, and patent applications cited herein are incorporated herein by reference to the same extent that the entirety of each document is specifically described.

The present invention has been described hereinafter while showing preferred embodiments to facilitate understanding. While the present invention is explained hereinafter based on Examples, the above explanations and the following Examples are provided for the sole purpose of exemplification, but not limitation of the present invention. Thus, the scope of the present invention is not limited to the embodiments and Examples that are specifically described herein and is limited only by the scope of claims.

EXAMPLES

Example 1: Sorting of Mutant Peptides and Examining Immunogenicity—for Tumor in Human Subject (Analysis)

Figure 2:
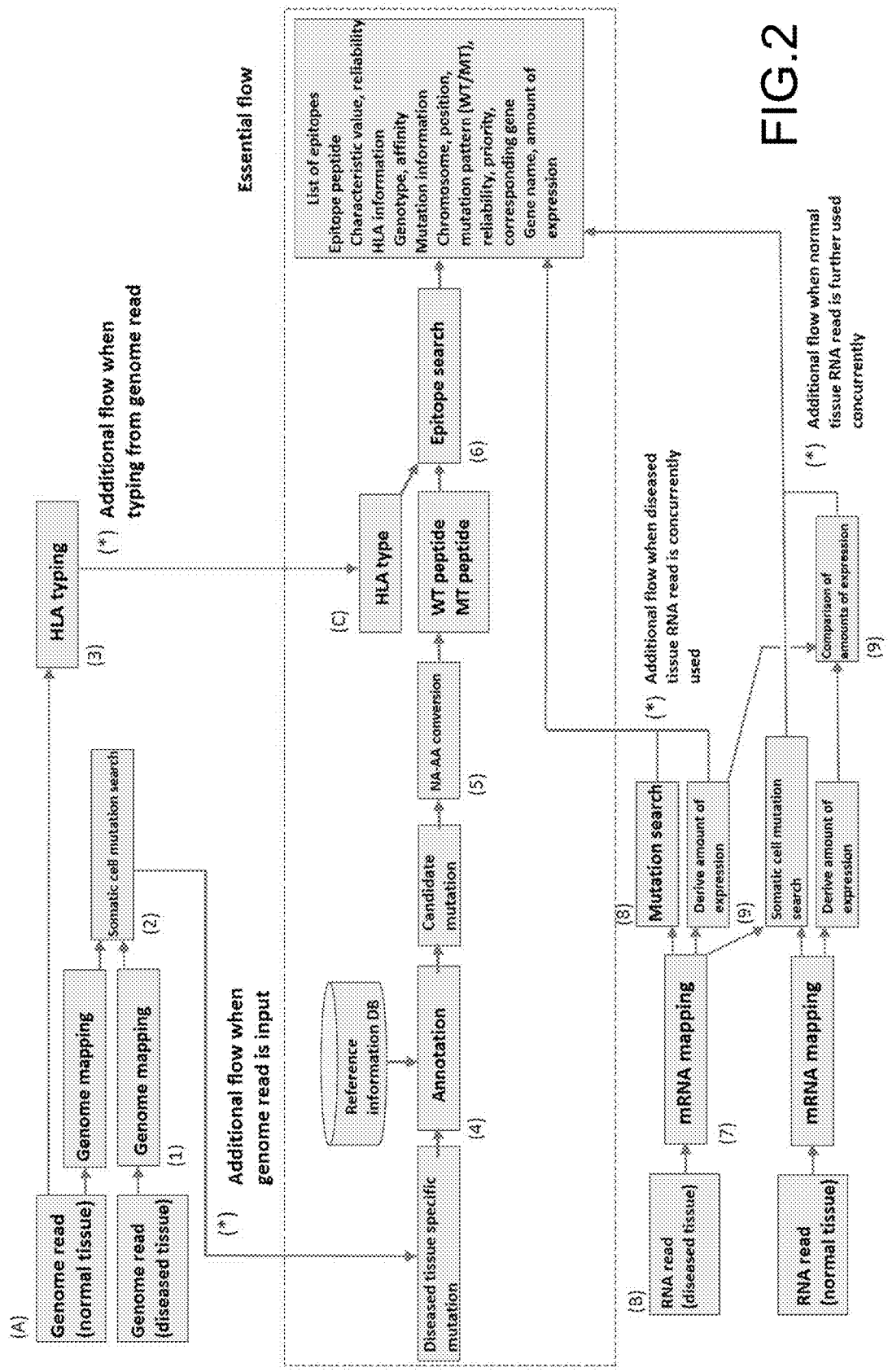
FIG. 2 depicts a schematic diagram of the analysis flow. The dotted line in the center indicates the core flow in the present invention. The region outside of the dotted line indicates optional additional analysis steps.

Mutant peptides were sorted based on the flow exemplified in FIG. 2.

Specifically, the following was performed.

(1) The following group of subjects was used.

Target patients: 65 year old Japanese male lung cancer patients

Before conducting the Example, the following HLA types were identified by typing using the Luminex assay.

HLA type: HLA-A*02:01, 24:02

(2) DNA was extracted from a normal tissue and a tumor tissue. Exome sequencing was performed with Illumina's sequencer HiSeq 2000 using a TruSeq PE kit. The equipment used was Illumina's sequencer HiSeq 2000, and the software used was the control software of the same sequencer.

(Exome Read Mapping)

Next, exome reads from a normal tissue and tumor tissue were each mapped with the following parameters using bwa.

algorithm: mem
read mode: paired end
minimum seed length: 19
band width: 100
off diagonal dropoff: 100
match score: 1
mismatch penalty: 4
gap open penalty: 6
gap extension penalty: 1
clipping penalty: 5
unpaired read penalty: 9

(Somatic Cell Mutation Search)

Next, a tumor tissue specific somatic cell mutation was searched using muTect, VarScan, and lofreq based on results of mapping exome reads from a normal tissue and tumor tissue.

Figure 3:
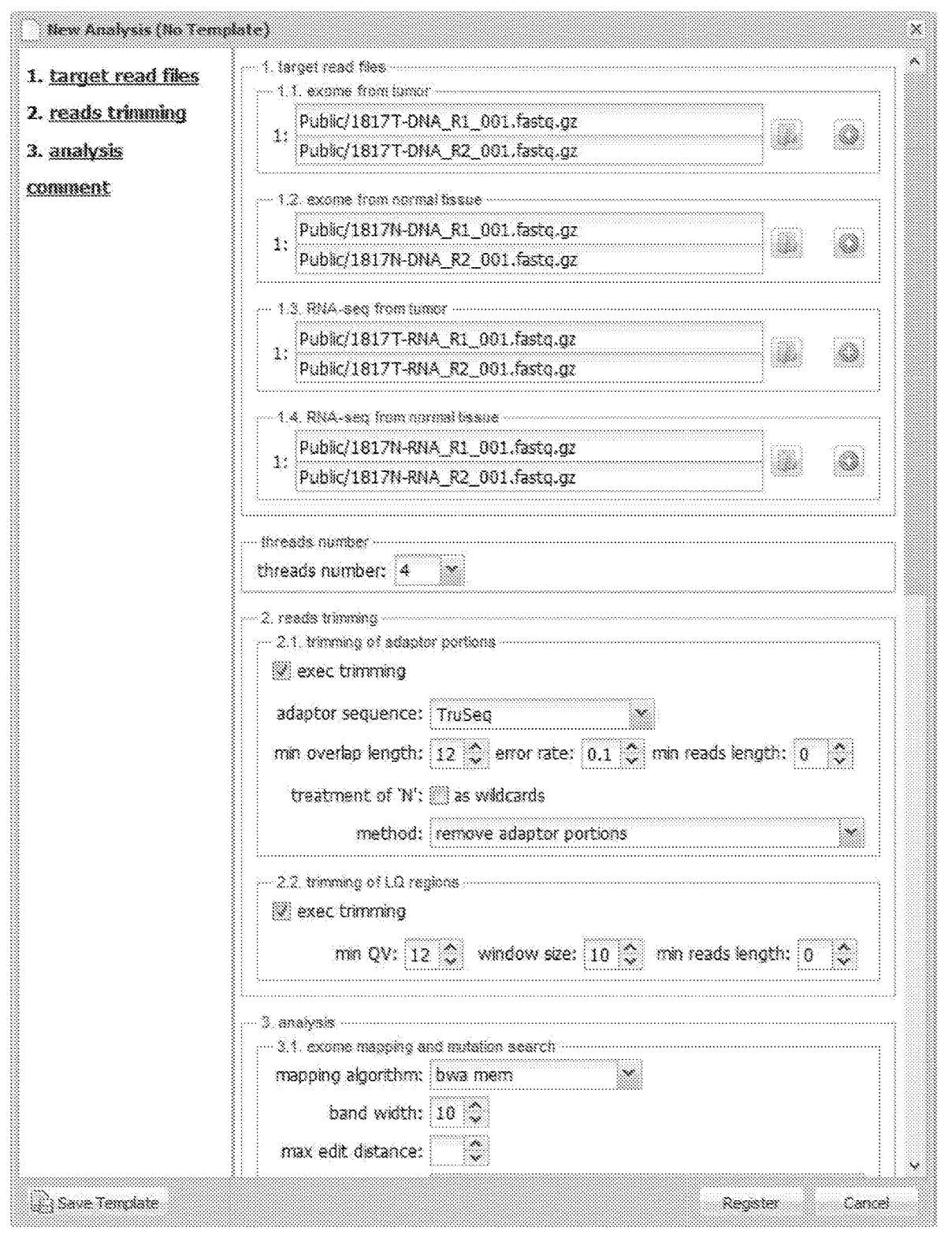
Figure 5:
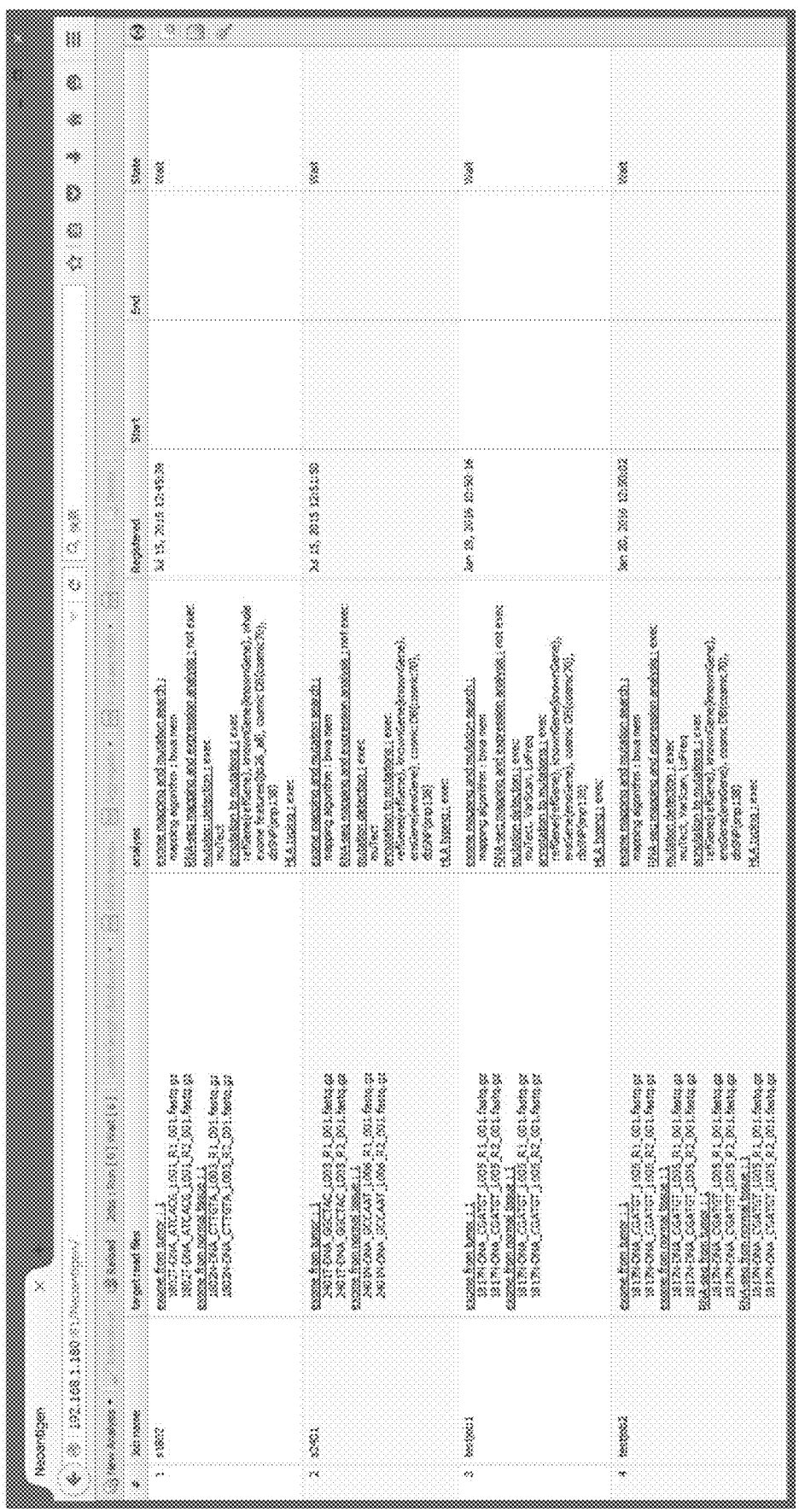
FIG. 5 is an example of output results.

The above analysis materialization flow is shown in FIGS. 3 to 5. FIG. 3 shows a start screen in an analysis flow, where an exome from tumor, exome from normal tissue, RNA sequence from tumor, RNA sequence from normal tissue, number of threads, read trimming conditions, trimming of low quality (LQ) region, analysis conditions, and the like can be selected. For example, the type of algorithm such as mapping algorithm and the conditions thereof can be selected and set for analysis conditions. FIG. 4 shows an analysis condition setting screen. Conditions for exome mapping and mutation search, RNA mapping and expression analysis thereof, mutation detection, annotation for mutations, HLA typing, and software and conditions used for epitope prediction (determination) can be selected and set. FIG. 5 is an example of output results. As a result, tumor specific mutations were counted and 1673 mutations were found.

(3) Next, RNA reads (normal tissue) and RNA reads (tumor tissue) were obtained. RNA was extracted from a tumor tissue and sequenced with Illumina's sequencer HiSeq 2000 using a TruSeq RNA Library kit and TruSeq PE kit. The obtained RNA reads were mapped using TopHat with the following parameters.

segment length: 16
maximum mismatch: 2
expected mate pair inner distance: 50
standard deviation of mate pair inner distance: 20

(4) Next, data obtained as a result of mRNA mapping was used to search for a mutation (or search for a somatic cell mutation) and derive the amount of expression. A mutation was searched using muTect and VarScan based on the result of mapping RNA reads from a tumor tissue. The amount of gene expression was also calculated using Cufflinks.

(5) The results based on RNA reads obtained in (4) with a mutation were analyzed together.

(6) Annotations were added for the tumor specific mutations obtained in (2) using refGene and ensEmbl as a database of gene structure information to identify candidate mutations. The identified candidate mutations were subjected to nucleic acid-amino acid conversion to define wild-type (WT) and mutant (MT) peptides.

(7) Next, HLA typing was performed using omixon from the exome reads.

(8) Epitopes were analyzed with information on HLA types together with the WT and MT peptides obtained in (6). The results thereof are shown in the following Table. The hyphens in the MT sequences in the Table indicate that the amino acids at the end thereof or therebetween are mutated compared to normal amino acids.

The sections in the Table indicate the following.

HLA allele: HLA allele
WT peptide sequence: wild-type peptide sequence
MT peptide sequence: mutant peptide sequence
Consensus percentile rank: consensus percentile rank
ANN IC50: IC50 calculated using artificial neural network method (optimal value in NetMHCpan)
ANN rank: value thereof converted into a rank value
SMM IC50: IC50 calculated using stabilized matrix method (na when a value cannot be calculated)
SMM rank: value thereof converted into a rank value
comblib sydney2008 score: IC50 calculated using sydney2008 method (na when a value cannot be calculated)
comblib sydney2008 rank: value thereof converted into a rank value
mutation information: mutation information
chromosome: chromosome start position: start position
end position: end position
gene name: gene name
accession: accession number
exon ID: exon number
position on transcript: position on transcript
WT NA: nucleic acid in wild-type
MT NA: nucleic acid in mutant
start pos. on peptide: start position on peptide
mutation pos. on peptide: mutation position on peptide
end pos. on peptide: end position on peptide
WT AA: wild-type amino acid
MT AA: mutant amino acid
upstream AA: upstream amino acid
downstream AA: downstream amino acid
log likelihood: log likelihood
read depth: read depth
num of WT on tumor: number of WT (no mutation) reads covering the position in tumor tissue
num of MT on tumor: number of MT (mutation) reads covering the position in tumor tissue
QV sum of WT on tumor: sum of quality values (QV) of WT reads covering the position in a tumor tissue
QV sum of MT on tumor: sum of quality values (QV) of MT reads covering the position in a tumor tissue
num of WT on normal: number of WT reads covering the position in a normal tissue
num of MT on normal: number of MT reads covering the position in a normal tissue
QV sum of WT on normal: sum of QV of WT reads covering the position in a normal tissue
QV sum of MT on normal: sum of QV of MT reads covering the position in a normal tissue
found in RNA: flag for whether the mutation was also found in RNA
found by: list of software that has found the mutation
all AA changes: description of amino acid substitution pattern with gene name, accession of locus, nucleic acid mutation pattern, or amino acid mutation pattern
cytoband: the position shown in cytoband file format
dbSNP 138: ID of the mutation when registered in dbSNP release.138
cosmic 70: ID of the mutation when registered in cosmid release.70
TSS: ID of TSS (Transcription Start Site) of a gene where the mutation is
gene location on genome: simply linking the position of the mutation, chromosome, start position, and end position
gene expression (FPKM): amount of gene expression (fragments per kilobase of exon per million mapped reads)
95% conf low: lower limit of 95% confidence interval for FPKM
95% conf high: upper limit of 95% confidence interval for FPKM
status: whether the result of calculating the amount of expression is effective (OK) or low precision (LOWQUAL)

TABLE 1-1

| HLA allele | WT peptide sequence | Consenus percentile rank | ANN IC50 | ANN rank | SMM IC50 | SMM rank | Comblib sydney 2008 score | Comblib sydney 2008 rank |
|---|---|---|---|---|---|---|---|---|
| HLA-C±03:03 | L-ANFVLQDQLAL (SEQ ID NO: 1) | 1.1 | 14 | 1.1 | na | na | na | na |
| HLA-C±03:03 | IA-Q-RSVIL (SEQ ID NO: 2) | 0.5 | 7 | 0.5 | na | na | na | na |
| HLA-C±14:02 | TYPAAHHFR-I-GI (SEQ ID NO: 3) | 0.2 | 6 | 0.2 | na | na | na | na |

| HLA allele | MT peptide sequence | Consensus percentile rank | ANN IC50 | ANN rank | SMM IC50 | SMM rank | Comblib sydney 2008 score | Comblib sydney 2008 rank |
|---|---|---|---|---|---|---|---|---|
| HLA-C±03:03 | F-ANFVLQDQLAL (SEQ ID NO: 4) | 0.3 | 3 | 0.3 | na | na | na | na |
| HLA-C±03:03 | IA-L-RSVIL (SEQ ID NO: 5) | 0.3 | 3 | 0.3 | na | na | na | na |
| HLA-C±14:02 | TYPAAHHFR-S-GI (SEQ ID NO: 6) | 0.1 | 4 | 0.1 | na | na | na | na |

TABLE 1-2

| | | mutation information | | | | |
|---|---|---|---|---|---|---|
| HLA allele | MT peptide sequence | Chromosome | start position | end position | gene name | accession |
| HLA-C*03:03 | F-ANFVLQDQLAL (SEQ ID NO: 4) | 6 | 10529961 | 10529961 | GCNT2 | NM_145649 |

TABLE 1-2-continued

| HLA allele | | | | | | |
|---|---|---|---|---|---|---|
| HLA-C*03:03 | IA-L-RSVTL (SEQ ID NO: 5) | 1 | 55073635 | 55073635 | ACOT11 | NM_015547 |
| HLA-C*14:02 | TYPAAHHFR-S-GI (SEQ ID NO: 6) | 6 | 1.10E+08 | 1.10E+08 | SMPD2 | NM_003080 |

| HLA allele | exon ID | position on transcript | WT NA | MT NA | start pos. on peptide | mutation pos. on peptide | end pos. on peptide | WT AA | MT AA |
|---|---|---|---|---|---|---|---|---|---|
| HLA-C*03:03 | exon3 | 817 | T | C | 260 | 273 | 286 | F | L |
| HLA-C*03:03 | exon15 | 1523 | T | A | 495 | 508 | 521 | L | Q |
| HLA-C*14:02 | exon3 | 224 | G | T | 62 | 75 | 88 | S | I |

TABLE 1-3

| HLA allele | upstream AA | WT AA | MT AA | downstream AA | log likelihood | read depth num of WT on tumor | num of MT on tumor |
|---|---|---|---|---|---|---|---|
| HLA-C*03:03 | IYFGTAYVALTRD (SEQ ID NO: 7) | F | L | ANFVLQDQLALDL (SEQ ID NO: 10) | 169.489 | 147 | 51 |
| HLA-C*03:03 | RKPCDNGDPYVIA (SEQ ID NO: 8) | L | Q | RSVTLPTHRETPE (SEQ ID NO: 11) | 69.688 | 85 | 22 |
| HLA-C*1402 | KLSPTYPAAHHFR (SEQ ID NO: 9) | S | I | GIIGSGLCVFSKH (SEQ ID NO: 12 | 168.897 | 143 | 51 |

| HLA allele | QV sum of WT on tumor | QV sum of MT on normal | num of WT on mormal | num of MT on normal | QV sum of WT on normal | QV sum of MT on normal |
|---|---|---|---|---|---|---|
| HLA-C*03:03 | 5548 | 1942 | 190 | 0 | 7217 | 0 |
| HLA-C*03:03 | 3194 | 828 | 105 | 0 | 3892 | 0 |
| HLA-C*1402 | 5406 | 1931 | 174 | 1 | 6576 | 40 |

TABLE 1-4

| HLA allele | downstream AA | found in RNA | found by | All AA changes |
|---|---|---|---|---|
| HLA-C*03:03 | ANFVLQDQLALDL (SEQ ID NO: 10) | found | muTect, VarScan, 1of req | GCNT2:NM_145649:exon3:c.T817C:p.F273L |
| HLA-C*03:03 | RSVTLPTHRETPE (SEQ ID NO: 11) | found | muTect, VarScan, 1of req | ACOT11:NM_015547:exon15:c.T1523A: p.L508Q,ACOT11:NM_147161:exon15: c.T1523A:p.L508Q |
| HLA-C*14:02 | GIIGSGLCVFSKH (SEQ ID NO: 12) | found | muTect, VarScan, 1of req | SMPD:NM_003080:exon3:c.G224T:p.S751 |

TABLE 1-5

| HLA allele | Downstream AA | cytoband | dbSNP 138 | cosmic 70 | gene name | TSS |
|---|---|---|---|---|---|---|
| HLA-C*03:03 | ANFVLQDQLALDL (SEQ ID NO: 10) | 6p24.3 | NA | NA | GCNT2 | TSS21103, TSS22414, TSS24961 |
| HLA-C*03:03 | RSVTLPTHRETPE (SEQ ID NO: 11) | 1p32.3 | NA | NA | ACOT11 | TSS26838 |
| HLA-C*14:02 | (SEQ ID NO: 12) GIIGSGLCVFSKH | 6q21 | NA | NA | SMPD2 | TSS22029 |

| HLA allele | gene location on genome | gene expression (FPKM) | | | status |
|---|---|---|---|---|---|
| | | FPKM | 95% conf low | 95% conf high | |
| HLA-C*03:03 | chr6:10521567-10629601 | 3.82342 | 3.46133 | 4.18551 | OK |
| HLA-C*03:03 | chr1:55013806-55100417 | 1.35652 | 0.97728 | 1.73576 | OK |
| HLA-C*14:02 | chr6:109761930-109765122 | 4.63929 | 3.85439 | 5.4242 | OK |

(Analysis Result)

The results of analysis are shown below.

1673 tumor specific mutations were found from the analysis using individuals of HLA-A*02:01, 24:02. The mutations were narrowed down to 41 by identifying cases that also had a mutation on an RNA read. These were narrowed down to 25 when narrowed down to mutations that further had an amino acid change. When counted by the number of peptides, 44 peptides were identified (HLA-A*02:01). In other words, 44 peptides having affinity of IC50 54 nM to HLA-A*02:01 were found. In the next step, peripheral blood of healthy individuals with HLA-A*02:01 was used, so that only peptides with affinity to HLA-A*02:01 (instead of HLA-A*24:02) were selected.

(Peptide Synthesis)

These 44 peptides were synthesized with a peptide synthesizer. In this Example, the procedure thereof is shown below. Peptides outsourced to GenScript (Tokyo, Japan) were used.

(HLA-A*02:01 Sample)

Peripheral blood of healthy individuals with the same HLA-A*02:01 as the subject sample (tumor patient) was used. An experiment of reactivity was conducted using peptides that were manufactured therefor.

Blood (peripheral blood) of healthy individuals with the same HLA type (e.g., HLA-A*02:01) or the blood of cancer patients itself can be used as the sample. Blood of those with the same HLA-A*02:01 can also be used depending on the objective.

(ELISPOT Assay)

The conducted assay performed interferon γ ELISPOT and intracellular interferon γ staining. For the interferon γ ELISPOT, MABTECH anti-human IFN-γ mAb 1-D1K, purified (3420-3-250) was used as a capture antibody. In addition, MILLIPORE MultiScreen HTS 96-well Filtration Plate was used.

Briefly stated, the following was performed.

(1) Cytokine (interferon-γ in this example) specific monoclonal antibodies (MABTECH anti-human IFN-γ mAb 1-D1K, purified (3420-3-250)) were immobilized on the solid layer surface. MILLIPORE MultiScreen HTS 96-well Filtration Plate was used in this example.

(2) $1\times10^5$ cells were stimulated and cultured for 16 hours after washing. The secreted cytokines, i.e., interferon-γ, were bound to capture antibodies (Detection antibody; MABTECH anti-human IFN-γ mAb 7-B6-1, biotinylated (3420-6-250)) that were around the producing cells. After removing the cells by washing, anti-interferon γ antibodies for detection were added.

For biotin labeled detection antibodies, enzyme labeled streptavidin (MABTECH Streptavidin-HRP (3310-9)) was added.

(3) Next, BD ELISPOT AEC Substrate Set (551951) was used for coloration. This method allows the spot corresponding to the position where interferon γ (cytokine) producing cell was located to be seen. The obtained spots were counted with a Carl Zeiss KS ELISPOT (Minerva Tech). The frequency of positive cells was recorded.

(Intracellular Interferon γ Staining)

The obtained samples were subjected to intracellular interferon γ staining. $5\times10^5$ lymphocytes were stimulated and cultured for 4 hours in a 200 μl medium. Neoantigen peptides and control peptides were added so that the final concentration was 1 μg/ml for stimulation. An unstimulated control was also prepared. BioLegend Brefeldin A Solution (1,000×) was added so that the final concentration would be 5.0 μg/ml during stimulation. After the completion of culturing, the cells were collected and stained for 30 minutes at 4° C. with Fixable Viability Dye eFluor780 (eBioscience 65-0865-18), FITC labeled anti-CD4 antibody (BD Pharmingen™557307), ECD labeled anti-CD8 antibody (BECKMAN COULTER 41116015) and PerCP-CY5.5 labeled anti-CD3 antibody (Biolegend 300430).

The cells were treated for 15 minutes with Intraprep permeabilization reagent (Immunotech, Marseille, France). The cells were stained for 15 minutes with PE labeled anti-IL-2 antibody (BD Pharmingen™559334), Alexa700 labeled anti-TNFα antibody (BD Pharmingen™557996), and Pacific Blue labeled anti-IFN-γ antibody (Biolegend 502522)

After suspension into PBS containing 0.5% PFA, measurement was taken with Gallios flow cytometer (BECK- MAN COULTER). For intracellular flow cytometry sorting, CD8 positive cells were used to analyze the production of interferon γ.

(Results for Interferon γ Production)

FIG. 6 shows the results of analyzing interferon γ production. Mutant peptides found to produce interferon γ for various peptides are summarized below in Table 2 (MT sequences listed as pepID 14, 21, 41, 36, 7, 43, 30, 33, 42, 27, 12, and 18 are SEQ ID NOS: 13-24 respectively, and WT sequences listed as pepID 14, 21, 41, 36, 7, 43, 30, 33, 42, 27, 12, and 18 are SEQ ID NOS: 25-36 respectively). In Table 2, amino acids with a change were underlined.

TABLE 2

| pepID | sequence MT | WT | IC50 MT | IC50 WT | IFNγ secretion ELISPOT | IFNγ secretion Intra |
|---|---|---|---|---|---|---|
| 14 | FLALECLAHL | SLALECLAHL | 0.25 | 0.95 | ++ | ++ |
| 21 | QLLEPEISFL | QLLEPQISFL | 1.1 | 1.35 | − | ++ |
| 41 | FTYSSALKV | FRYSSALKV | 1.4 | 12 | ++ | ++ |
| 36 | ILQEYREDFV | IRQEYREDFV | 2.3 | 38.5 | − | + |
| 7 | VLNINDNEPV | VLDINDNEPV | 2.35 | 1.65 | − | ++ |
| 43 | FQYSSPALPT | YQYSSPALPT | 3.2 | 3.7 | ++ | − |
| 30 | ALYPFEFRS | ALYPFESRS | 3.9 | 9.2 | − | + |
| 33 | NISSRIHTV | NISSHIHTV | 4.1 | 3 | + | ++ |
| 42 | KTFTYSSAL | KTFRYSSAL | 4.1 | 5.6 | ++ | − |
| 27 | KVLQLLEPEI | KVLQLLEPQI | 4.5 | 6.3 | − | + |
| 12 | NLKKLLVF | NLEKLLVF | 17 | 16 | ++ | − |
| 18 | ICFLALECLAH | ICSLALECLAH | 54 | 71.5 | ++ | − |

In the Table, MT indicates a mutant, and WT indicates a wild-type. pepID is the sample number in the Example. IC50 indicates the concentration inhibiting HLA-peptide binding. In the Table, ++ refers to a sample found to produce interferon γ in 3/3, and + refers to a sample found to produce interferon γ in 1/3 to 2/3.

It was revealed from the above that a positive reaction was observed for ELISPOT or intracellular interferon production in 12 cases, which is nearly 30% of the 44 cases found in the example.

A candidate cancer immunopeptide that can be useful has never been found in nearly 30% of cases in conventional art. Thus, this is considered a significant effect.

Example 2: Sorting of Mutant Peptides and Examining Immunogenicity—for Mice

In this Example, the same experiment can be conducted when using mice.

The procedure thereof is shown below.

1. Neoantigens can be searched in spontaneously, chemically, and radiation induced tumor (cancer, sarcoma, or leukemia) in mouse of all strains (syngenic). In this Example, mouse strain: C57BL/6 (MHC Haplotype H2$^b$) is used. Tumor: B16 melanoma cells are used as the tumor.
2. Tissue is collected from a cancerous site in a cancer bearing mouse, and the same organ/tissue as the tumor site is collected in a normal mouse, where a tumor site and non-tumor site (e.g., tumor site and non-tumor site for colon cancer) are collected in the cancer bearing mouse. When the mice are from the same strain, normal tissue is collected from the normal mouse.
3. DNA and RNA are extracted from the collected tissue/organ to perform exome seq and RNA seq analysis.
4. Since the MHC (major histocompatibility complex) is known for each strain, the mutanome is searched, and then neoantigens presented on the MHC (H-2 in mice) are identified.
5. For selection of neoantigens, the same methodology as that described for human tumor in Example 1 is used. Specifically, normal skin is collected from a C57BL/6 mouse syngenic to B16 melanoma cells, DNA and RNA are extracted therefrom, exome seq/RNA seq is performed, and candidate peptides are identified with the neoantigen searching software in Example 1.
6. For the identified neoantigens, a peptide is artificially synthesized, and added and cultured in spleen cells of syngenic mouse to use induction of IFNγ production after culturing as an indicator of activity.
7. The spleen cells that have been stimulated with neoantigens and cultured are used to measure cytotoxicity to tumor.
8. It is clarified that searched neoantigens functionally induce T cells against tumor from studying the content of a test tube.
9. The in vivo effect using the candidate neoantigens is examined.
10. As the in vivo effect, neoantigens are directly administered to a cancer bearing mouse (mouse to which tumor used in neoantigen search is transplanted). Further, dendritic cell therapy (dendritic cells from syngenic mice are stimulated and cultured in vitro and administered to the cancer bearing mice) can be used for therapy.

The effect is determined as follows.

1. The effect is determined in vivo after an Elispot assay using C57Bl/6 mouse derived spleen cells and verification of cytotoxicity.
2. B16 melanoma cells are subcutaneously transplanted in C57BL/6 mice (1×10$^6$). The same number of B16 melanoma cells is intravenously injected.
3. After the B16 subcutaneous administration, the size of tumor and survival rate are used as an indicator for the therapeutic effect of neoantigens.

In this manner, antigen peptides can also be identified for treatment in mice.

As disclosed above, the present invention is exemplified by the use of its preferred embodiments. However, it is understood that the scope of the present invention should be interpreted based solely on the Claims. It is also understood that any patent, any patent application, and any references cited herein should be incorporated herein by reference in the same manner as the contents are specifically described herein. The present application claims priority to Japanese Patent Application No. 2016-50861 (filed on Mar. 15, 2016). The entire content thereof is incorporated herein by reference.

INDUSTRIAL APPLICABILITY

A technology for identifying an immunotherapeutic peptide with high accuracy is provided, enabling therapy, monitoring and prevention with a higher precision. The technology is particularly useful in the pharmaceutical industries and clinical settings.

SEQUENCE LISTING FREE TEXT

SEQ ID NOs: 1 to 12 are amino acid sequences disclosed in the results of the epitope analysis with information on HLA types together with the WT and MT peptides performed in Example 1. SEQ ID NOs: 1, 4, 7, and 10 are the sequences displayed in the first sample (HLA-C*03:03). SEQ ID NOs: 2, 5, 8, and 11 are sequences displayed in the second sample (HLA-C*03:03). SEQ ID NOs: 3, 6, 9, and 12 are sequences displayed in the third sample (HLA-C*14:02). SEQ ID NOs: 1 to 3 indicate wild-type amino acid sequences, SEQ ID NOs: 4 to 6 indicate mutant amino acid sequences, SEQ ID NOs: 7 to 9 indicate upstream amino acid sequences, and SEQ ID NOs: 10 to 12 indicate downstream amino acid sequences. SEQ ID NOs: 13 to 36 indicate amino acid sequences of peptides that actually had a hit shown in Table 2. SEQ ID NOs: 13 to 24 are mutant amino acid sequences that indicate, in order, PepID 14, 21, 41, 36, 7, 43, 30, 33, 42, 27, 12, and 18. SEQ ID NOs: 25 to 36 are wild-type amino acid sequences that indicate, in order, PepID 14, 21, 41, 36, 7, 43, 30, 33, 42, 27, 12, and 18.

The invention claimed is:

1. A method of producing a peptide for treating, monitoring, or diagnosing a disease in a subject, the method comprising the steps of:
   A) inputting into an analyzer information related to a mutation specific to a diseased tissue of the subject and information on an MHC type of the subject, wherein the step A) comprises the steps of:
      A-1) making the analyzer sequence a genome of the subject to obtain and map the information related to a genome read of the subject and the mutation thereof, and then search for the mutation specific to the diseased tissue to obtain the mutation specific to the diseased tissue; and
      A-2) making the analyzer sequence an RNA of the subject to obtain information on an RNA read of the subject, map an RNA read of the diseased tissue, and search for a mutation, and/or derive an amount of expression, and map an RNA read of a normal tissue to search for a somatic cell mutation and/or derive an amount of expression to compare said amount with the amount of expression derived based on the RNA read of the diseased tissue;
   B) making the analyzer analyze an epitope associated with the mutation based on the information related to the mutation specific to the diseased tissue, the information on the MHC type, and information on the disease,
   wherein the step B) comprises the step of making the analyzer add an annotation for the mutation specific to the diseased tissue based on a reference information database to identify a candidate mutation, wherein nucleic acid information of the candidate mutation is then converted to amino acid information to produce a wild-type (WT) peptide and a mutant (MT) peptide, and then the analyzer is made to search for an epitope using the MHC type, the WT peptide, and the MT peptide after which epitopes are ranked, and to output an epitope list;
   wherein the ranking is performed by taking into consideration at least one element selected from the group consisting of prioritization of the mutation, presence/absence of gene expression, and prioritization of a peptide; and
   wherein the ranking is sorted by applying, in order, a value of IC50 between HLA-peptide, the number of epitope searching programs which have found a hit, and the number of mutation searching softwares which have found a hit; and
   C) producing the peptide based on at least the epitope list output from the analyzer in accordance with the ranking of step B).

2. The method of claim 1, comprising deriving the mutation specific to the diseased tissue based on the information related to a genome read of the subject and the mutation thereof.

3. The method of claim 1, wherein the step A) further comprises inputting information on an RNA read of the subject into the analyzer, and the step B) comprises making the analyzer analyze an epitope associated with the mutation based on the information on the RNA read.

4. The method of claim 1, wherein the MHC type is derived from a genome read of the subject.

5. The method of claim 1, wherein the step A) further comprises the step of:
   A-3) making the analyzer perform MHC typing of the subject using the genome read of the subject to obtain information on the MHC type of the subject.

6. An apparatus that produces a peptide for treating, monitoring, or diagnosing a disease in a subject, the apparatus comprising a non-transitory computer-readable medium, and further comprising:
   A) an information inputting unit for inputting information related to a mutation specific to a diseased tissue of the subject wherein the information inputting unit comprises means for sequencing a genome of the subject, means for determining the mutation specific to the diseased tissue of the subject, and means for sequencing an RNA of the subject;
   B) an epitope analyzing unit for analyzing an epitope associated with the mutation based on the information related to the mutation specific to the diseased tissue of the subject,
   wherein the epitope analyzing unit adds an annotation for the mutation specific to the diseased tissue based on a reference information database to identify a candidate mutation, wherein nucleic acid information of the candidate mutation is then converted to amino acid information to produce a wild-type (WT) peptide and a mutant (MT) peptide, and then the epitope analyzing unit is made to search for an epitope using the MHC type, the WT peptide, and the MT peptide after which epitopes are ranked, and to output an epitope list;
   wherein the ranking is performed by taking into consideration at least one element selected from the group consisting of prioritization of the mutation, presence/absence of gene expression, and prioritization of a peptide; and
   wherein the ranking is sorted by applying, in order, a value of IC50 between HLA-peptide, the number of epitope searching programs which have found a hit, and the number of mutation searching softwares which have found a hit; and C) a peptide producing unit that produces the peptide based on at least the epitope list output from the epitope analyzing unit in accordance with the ranking in B).

7. The apparatus of claim 6, wherein the information inputting unit further comprises means for MHC typing the subject.

8. A computer readable recording medium storing a program for making a computer execute a method of identifying a peptide for treating, monitoring, or diagnosing a disease in a subject, the method comprising the steps of:
A) inputting information related to a mutation specific to a diseased tissue of the subject, wherein the step A) comprises the steps of:
  A-1) making the computer sequence a genome of the subject to obtain and map the information related to the genome read of the subject and the mutation thereof, and then search for the mutation specific to the diseased tissue to obtain the mutation specific to the diseased tissue; and
  A-2) making the computer sequence an RNA of the subject to obtain information on an RNA read of the subject, map an RNA read of the diseased tissue, and search for a mutation, and/or derive an amount of expression, and map an RNA read of a normal tissue to search for a somatic cell mutation and/or derive an amount of expression to compare said amount with the amount of expression derived based on the RNA read of the disease tissue;
B) analyzing an epitope associated with the mutation based on the information related to the mutation specific to the diseased tissue of the subject, and outputting a result thereof as a peptide for treating, monitoring, or diagnosing the disease,
wherein the step B) comprises the step of making the computer add an annotation for the mutation specific to the diseased tissue based on a reference information database to identify a candidate mutation, wherein nucleic acid information of the candidate mutation is then converted to amino acid information to produce a wild-type (WT) peptide and a mutant (MT) peptide, and then the computer is made to search for an epitope using the MHC type, the WT peptide, and the MT peptide after which epitopes are ranked, and to output an epitope list;
wherein the ranking is performed by taking into consideration at least one element selected from the group consisting of prioritization of the mutation, presence/absence of gene expression, and prioritization of a peptide; and
wherein the ranking is sorted by applying, in order, a value of IC50 between HLA-peptide, the number of epitope searching programs which have found a hit, and the number of mutation searching softwares which have found a hit; and
C) producing the peptide based on at least the epitope list output in accordance with the ranking in step B).

* * * * *